US012605079B2

(12) United States Patent
Post

(10) Patent No.: US 12,605,079 B2
(45) Date of Patent: Apr. 21, 2026

(54) SYSTEM AND A METHOD OF DETERMINING A PHYSIOLOGICAL PARAMETER OF A BODY COMPRISING BLOOD PERFUSED TISSUE

(71) Applicant: Sonion Nederland B.V., Hoofddorp (NL)

(72) Inventor: Peter Christiaan Post, Hoofddorp (NL)

(73) Assignee: Sonion Nederland B.V., Hoofddorp (NL)

( * ) Notice: Subject to any disclaimer, the term of this patent is extended or adjusted under 35 U.S.C. 154(b) by 0 days.

(21) Appl. No.: 19/252,895

(22) Filed: Jun. 27, 2025

(65) Prior Publication Data

US 2025/0325196 A1 Oct. 23, 2025

Related U.S. Application Data

(63) Continuation of application No. PCT/EP2024/059669, filed on Apr. 10, 2024.

(30) Foreign Application Priority Data

Apr. 14, 2023 (EP) ..................................... 23168018
Oct. 17, 2023 (EP) ..................................... 23204053

(51) Int. Cl.
*A61B 5/021* (2006.01)
*A61B 5/00* (2006.01)

(52) U.S. Cl.
CPC ............ *A61B 5/021* (2013.01); *A61B 5/6801* (2013.01); *A61B 5/7239* (2013.01); *A61B 2560/0462* (2013.01); *A61B 2562/0233* (2013.01)

(58) Field of Classification Search
CPC ..... A61B 5/021; A61B 5/6801; A61B 5/7239; A61B 2560/0462; A61B 2562/0233
See application file for complete search history.

(56) References Cited

U.S. PATENT DOCUMENTS

2006/0211942 A1* 9/2006 Hoctor ............... A61B 5/02125
600/485
2008/0146890 A1 6/2008 LeBoeuf et al.
(Continued)

FOREIGN PATENT DOCUMENTS

KR 2019-0088751 A 7/2019
WO 2016/138965 A1 9/2016
(Continued)

OTHER PUBLICATIONS

Extended European Search Report dated Sep. 15, 2023 for Corresponding European Application No. 23168018.2.
(Continued)

*Primary Examiner* — Rene T Towa
(74) *Attorney, Agent, or Firm* — Harness, Dickey & Pierce, P.L.C.

(57) ABSTRACT

A system and a method for determining a physiological parameter of a body comprising blood perfused tissue, the system comprising a first sensor configured to receive first radiation from the blood perfused tissue and, based on the received first radiation, provide first information relating to an amount of blood in the tissue, such as from an absorption of the first radiation in the tissue, a second sensor configured to receive second radiation from the blood perfused tissue and, based on the received second radiation, provide second information relating to a speed of blood in the tissue, such as from Doppler shift of the second radiation, a controller configured to determine the physiological parameter from the first information and the second information.

13 Claims, 14 Drawing Sheets

(56)               References Cited

U.S. PATENT DOCUMENTS

| 2009/0112071 | A1  |         | 4/2009  | LeBoeuf et al.     |            |
|--------------|-----|---------|---------|--------------------|------------|
| 2010/0049017 | A1  |         | 2/2010  | LeBoeuf et al.     |            |
| 2010/0217098 | A1  |         | 8/2010  | LeBoeuf et al.     |            |
| 2011/0105874 | A1  |         | 5/2011  | Feddes et al.      |            |
| 2014/0114147 | A1  |         | 4/2014  | Romesburg          |            |
| 2015/0018636 | A1  |         | 1/2015  | Romesburg          |            |
| 2016/0106327 | A1  |         | 4/2016  | Yoon et al.        |            |
| 2017/0112447 | A1  |         | 4/2017  | Aumer et al.       |            |
| 2017/0209053 | A1* |         | 7/2017  | Pantelopoulos      | A61B 5/7278 |
| 2018/0235567 | A1* |         | 8/2018  | Bezemer            | A61B 5/02007 |
| 2019/0175030 | A1  |         | 6/2019  | Verkruijsse et al. |            |
| 2021/0353165 | A1* |         | 11/2021 | Galeev             | A61B 5/7264 |
| 2022/0133165 | A1  |         | 5/2022  | Proença et al.     |            |

FOREIGN PATENT DOCUMENTS

| WO | 2017/176781 | A1 | 10/2017 |
|----|-------------|----|---------|
| WO | 2018/029123 | A1 | 2/2018  |
| WO | 2023/031927 | A1 | 3/2023  |

OTHER PUBLICATIONS

International Search Report and Written Opinion dated Jul. 19, 2024 for Corresponding International Application No. PCT/EP2024/059669.

Garrett, Ariane, et al. "Simultaneous photoplethysmography and blood flow measurements towards the estimation of blood pressure using speckle contrast optical spectroscopy." Biomedical Optics Express 14.4 (2023): 1594-1607.

Ghijsen, Michael, et al. "Wearable speckle plethysmography (SPG) for characterizing microvascular flow and resistance." Biomedical optics express 9.8 (2018): 3937-3952.

Proença, Martin, et al. "PPG-based blood pressure monitoring by pulse wave analysis: calibration parameters are stable for three months." 2019 41st Annual International Conference of the IEEE Engineering in Medicine and Biology Society (EMBC). IEEE, 2019.

Solà, Josep, et al. "Continuous non-invasive monitoring of blood pressure in the operating room: a cuffless optical technology at the fingertip." Current Directions in Biomedical Engineering 2.1 (2016).

* cited by examiner

SYSTEM AND A METHOD OF DETERMINING A PHYSIOLOGICAL PARAMETER OF A BODY COMPRISING BLOOD PERFUSED TISSUE

CROSS-REFERENCE TO RELATED APPLICATIONS

This application is a continuation of PCT International Application No. PCT/EP2024/059669 which has an International filing date of Apr. 10, 2024, and which claims priority to European Patent Application No. 23168018.2, filed Apr. 14, 2023, and European Patent Application No. 23204053.5, filed Oct. 17, 2023, the entire contents of each of which are incorporated herein by reference.

BACKGROUND OF THE INVENTION

1. Field

The present invention relates to a system, apparatus and method for determining a parameter of blood flowing in blood perfused tissue, such as blood flowing below the skin of a person, such as in the wall of an ear canal of a person. The present invention further relates to a computer program for carrying out the method.

In particular, the invention relates to the determination of the parameter, based on information relating to both a blood speed, e.g. obtained from a laser Doppler velocimetry (LDV) sensor, and information related to a blood volume, e.g. obtained from a photoplethysmography (PPG) sensor.

2. Related Art

US20220133165 describes the determination of a physiological parameter that is related to the blood pressure from a waveform that is acquired by means of a PPG sensor by using peak detection in the $1^{st}$ and $2^{nd}$ time-derivative of the PPG waveform and extracting features from the PPG waveform using the $1^{st}$ and $2^{nd}$ time-derivative of the waveform based on the wave reflection theory of the arterial system.

It is known that PPG as a manner of obtaining biometrics has limitations:

It is sensitive to movement of the device/sensor relative to skin/tissue, e.g. during motion/exercise;

It is sensitive to ambient light and modulated ambient light; and

Its sensitivity deteriorates when vascular distensibility is decreased, mainly for elderly people and people with prevalence of hypertension.

Garrett, A. et al. [2023] Biomedical Optics Express, Vol. 14, No 1, pages 1594-1607 propose simultaneous photoplethysmography (PPG) and blood flow index (BFI) measurement to estimate blood pressure using speckle contrast optical spectroscopy. They correlated various features from PPG or BFI alone or a mathematical combination of BFI and PPG, such as a multiplication of diastolic time as determined from BFI pulse wave forms and systolic time as determined from PPG pulse wave forms. They found that for systolic blood pressure a mathematical combination of BFI and PPG pulse waveform correlated more strongly with blood pressure than PPG alone or BFI alone. For diastolic blood pressure, both BFI alone or PPG alone correlated more strongly with diastolic blood pressure as measured with an arm cuff. Although the study group mainly comprised young healthy subjects with medium skin tones, the correlation leaves much to be desired and is insufficient to reliably determine (systolic and diastolic) blood pressure instead of the known arm cuff method.

WO2023/031927 relates to a wearable physiological monitoring system comprising emitting coherent light in one or more wavelengths onto tissue of an examined subject at a measurement point; simultaneously detecting and determining with at least one light detector and a control unit a pulsating blood flow signal and a pulsating blood volume signal; and determining from both signals a local pulse wave velocity and determine from the local pulse wave velocity a blood pressure measure of the examined subject at the measurement point as a function of time. From a measured PPG signal, first-time derivatives of the PPG signal at two separate time points are determined and combined with an amplitude of a blood flow related pulse wave (PBFv(t)) in a mathematical model to arrive at a blood pressure measure. The model assumes a linear relationship between blood pressure and blood flow velocity which according to WO2023/031927 only applies during the first phase of increase of the PPG signal and the PBFv signal.

It would be desirable to be able to accurately measure both systolic and diastolic blood pressure. It would further be desirable to be able to accurately measure blood pressure in subjects with high blood pressure and/or with a low distensibility of blood vessels.

SUMMARY OF THE INVENTION

It is an object of the invention to improve the measurement of one or more physiological parameters, in particular blood pressure, systolic and diastolic blood pressure. In particular, the invention propose to use combined information related to blood volume, e.g. as obtained from a PPG sensor, with information related to a blood speed, e.g. as obtained from an LDV sensor or a speckle contrast optical spectroscopy sensor.

It has been found that PPG information may vary in quality depending on e.g. the distensibility of the blood vessels. In addition, the output of an LDV sensor will also depend on e.g. the distensibility, as a higher speed may be expected in blood vessels which are less flexible. By basing the estimation also on the further information, a more robust method is obtained and thus a better quality of the determined parameter.

Laser Doppler velocimetry (LDV) is also commonly referred to as laser Doppler flowmetry (LDF) when used for measuring blood flow in a body. The term 'velocimetry' suggests that velocity is measured but the blood flow signal obtained by LDV is in fact a scalar and contains no direction information. The blood flow signal is therefore in fact related to speed of the blood.

Since PPG measures a parameter related to the perturbation of the volume of blood in the tissue, and LDV measures a parameter related to the blood flow speed in, typically the arteries of, the blood perfused tissue, LDV cannot be a 1:1 replacement of PPG. Also, LDV may according to one embodiment be determined using radiation penetrating deeper into the tissue, to gain access to relatively larger blood vessels, relative to radiation used for the PPG, which may according to the one embodiment be determined at a shallower depth at the capillaries of the tissue.

Additionally, the blood flow speed is less affected by reduced vascular distensibility, and may be even increasing with reduced distensibility, so that the LDV signal does not deteriorate the same way as the sensitivity of PPG when vascular distensibility is decreased.

Thus, by combining PPG and LDV, or other information representing similar information, in e.g. a wearable device, such device may cover a wider range of users including elderly people and people with prevalence of hypertension where PPG may not function accurately.

In a first aspect, the invention relates to a system for determining a physiological parameter of a body comprising blood perfused tissue, the system comprising:

a first sensor configured to receive first radiation from the blood perfused tissue and, based on the received first radiation, provide first information relating to an amount of blood in the tissue, a second sensor configured to receive second radiation from the blood perfused tissue and, based on the received second radiation, provide second information relating to a speed of blood in the tissue, a controller configured to determine the physiological parameter from the first information and the second information.

According to one embodiment, the present invention provides a system for determining a physiological parameter of a body comprising blood perfused tissue, the system comprising:

a first sensor configured to receive first radiation from the blood perfused tissue and, based on the received first radiation, provide first information relating to an amount of blood in the tissue, a second sensor configured to receive second radiation from the blood perfused tissue and, based on the received second radiation, provide second information relating to a speed of blood in the tissue, a controller configured to calculate a first calculated signal from the second information and/or calculate a second calculated signal from the first information;

use the first calculated signal and the first information to calculate an improved first information and/or use the second calculated signal and the second information to calculate an improved second information; and determine the physiological parameter from the improved first information and/or improved second information.

Preferably, the controller is configured to calculate the first calculated signal using a model that predicts first information (related to an amount of blood in the tissue) from second information (related to a speed of blood in the tissue) and/or to calculate the second calculated signal using a model that predicts second information from first information. The first calculated signal thus relates to an amount of blood in the tissue, and the second calculated signal relates to a speed of blood in the tissue. The model may for example comprise a transfer function, a linear model, a non-linear model, a deterministic model or a non-deterministic model. To calculate the first calculated signal, the second information is provided as input to the model, and in response the model generates synthetic first information (i.e. predicted or estimated first information) as output. In other words, the first model converts second information into synthetic (predicted or estimated) first information. The synthetic first information generated by the model is then used to calculate the improved information. The improved first information relates to an amount of blood in the tissue, and the improved second information relates to a speed of blood in the tissue.

Similarly, to calculate the second calculated signal, the first information is provided as input to the model, and in response the model generates synthetic second information (i.e. predicted or estimated first information) as output.

The synthetic first information and/or synthetic second information may for example be computed by applying a transfer function to the second information and first information, respectively, as will be explained in detail below.

Although it is possible to use different models for calculating the first calculated signal and the second calculated signal, respectively, preferably a single model is used, such as an invertible model.

Preferably, the model comprises a transfer function based on a Windkessel model, as will be described below. Alternatively, the model comprises a computer-implemented neural network, such as a deep learning neural network with an input layer, and output layer and at least one hidden layer.

Preferably, the controller is configured to calculate the improved first information by adding the first calculated signal to the first information. Preferably, the addition comprises a weighted addition, i.e. a weighted sum.

Preferably, the controller is configured to calculate a synthetic time derivative of the first information and to calculate an improved first information from the synthetic time derivative of the first information and determine the physiological parameter from the improved first information. The calculation of the synthetic time derivative is explained in further detail below. Particularly, the first calculated signal may correspond to the synthetic time derivative of the first information.

Optionally, calculating the improved first information comprises integration of the synthetic time derivative of the first information. For example, the integral of the synthetic time derivative is computed and added to the first information, preferably by weighted addition, to obtain the improved first information.

According to another embodiment, the present invention provides a system for determining a physiological parameter of a body comprising blood perfused tissue, the system comprising:

a first sensor configured to receive first radiation from the blood perfused tissue and, based on the received first radiation, provide first information relating to an amount of blood in the tissue, a second sensor configured to receive second radiation from the blood perfused tissue and, based on the received second radiation, provide second information relating to a speed of blood in the tissue, a controller configured to calculate a synthetic time derivative of the first information from the second information and the first information; and determine the physiological parameter from the synthetic time derivative of the first information.

Preferably, the controller is configured to determine the physiological parameter from the synthetic time derivative of the first information and the first information.

In an embodiment, the controller is configured to calculate the synthetic time derivative of the first information using a model that predicts a time derivative of first information relating to an amount of blood in the tissue from first information relation to an amount of blood in the tissue and second information relating to a speed of blood in the tissue. Particularly, the output of the model depends both on the first information and the second information. For example, the model comprises a linear function of the first information and second information. The output of the model (i.e. the time derivative of the first information as predicted by the model) is then used as the synthetic time derivative.

Advantageously, in each of these embodiments of the first and second aspect, the controller is configured to determine blood pressure from the first and second information using a first-order or second-order Windkessel model.

The first and second information relate to different parameters of the body, so that the physiological parameter is based on additional information and not solely information relating to the amount of blood in the tissue or information relating solely to the speed of the blood in the tissue.

When the heart pumps blood through the blood vessels of a person, the blood vessels will expand and contract by the blood pressure pulses of the blood. Thus, the pulse generated by the heart will be extended in time and along the direction of the blood vessels. This will depend on also other parameters, such as the distensibility of the blood vessels. If these are not very flexible, the pulse will remain more concentrated in time so that the pulsed behaviour will be more prevalent also at a distance from the heart compared to a person with more flexible blood vessels. Also, reflections will be seen when the blood passes a bifurcation in the blood vessels, so the behaviour of the blood away from the heart may be quite complex but may, on the other hand, reveal a number of parameters of the blood vessels or cardiac system of the body.

Then, the physiological parameter may in principle relate to any parameter of the blood, the blood vessels or the cardiac system, such as (but not limited to) heart rate, heart rate variability, breathing rate, peripheral oxygen saturation ($SpO_2$), blood perfusion of the tissue, blood flow speed, blood pressure, arterial distensibility, user motion, and user activity.

The body may be a body of a person or an animal. In principle not only vertebrates such as mammals and avians may be relevant users, but at least larger mammals, such as horses, dogs, hounds or the like may benefit from the use of the present invention.

Blood perfused tissue is tissue which has a supply of blood, often via blood vessels provided in the tissue. The tissue may in principle be any tissue but will normally be tissue not too far from a surface or skin of the user, such as the tissue at or forming at least part of an ear canal, a portion of an ear, a finger, a limb, an arm, a leg, or the like of the body. The tissue may be tissue within 10 mm from a surface, such as the outer surface of skin, of the user, such as within 8 mm from the surface.

A sensor is an element which is configured to detect or sense a parameter and output a signal relating to the sensed parameter. Often, the output is correlated with the parameter so that when the parameter varies, the output of the sensor varies. A calibration may be provided from which a quantification of the parameter may be determined from a quantified output of the sensor. The output of the sensor may be analogue or digital and may be a simple signal, such as a voltage, a current, a sine signal or a pulsed signal, or parameter, such as a number, a frequency of a signal or the like, or may be a more complex signal, such as a series of numbers, a TDM signal, a value determined from a detector or the like.

In principle, the first and second sensors may share a radiation source and/or a detector. Embodiments exist wherein each sensor has a source and a detector. In other embodiments, the sensors have separate sources but share a detector, and it is also possible for the sensors to share a source and have separate detectors or share a detector. It is noted that, as mentioned below, the first sensor may not require a source at all, if the radiation is generated in the blood.

The first sensor is configured to receive first radiation from the blood perfused tissue and, based on the received first radiation, provide first information relating to an amount of blood in the tissue.

The amount of blood in the tissue may be quantified in a number of ways. In one method, a known amount of radiation is launched into the tissue, where some of the radiation is absorbed by the blood. The absorption may be caused by natural contents of the blood, such as the red blood cells, or may be absorbed by a component, such as a drug, added to the blood. Alternatively, the first radiation may be generated in or by the blood, such as when the blood comprises a radioactive, fluorescent or emitting component. When the absorbing, fluorescing or emitting component is evenly distributed in the blood, the intensity of received radiation correlates to the amount of blood in the tissue.

The first radiation may have any desired wavelength or combination of wavelengths depending on the way it is generated or interacts with the blood. If the first radiation is desirably absorbed by the blood, the wavelength may be selected to be one which a component of natural blood, or a component added to the blood, may absorb. Red blood cells typically absorb radiation in the interval 200-1000 nm.

When radiating, emitting or fluorescent agents are used, these are preferably biocompatible but may in principle be selected from a wide array of materials, where each material will define the wavelength(s) of the first radiation.

The second sensor is configured to receive second radiation from the blood perfused tissue. The output from this sensor enables the generation of second information relating to a speed of blood in the tissue. A widely used method of determining a speed of biological elements or components is based on the Doppler shift generated when the radiation such as light (or sound or ultrasound) is scattered by an element moving in relation to the sensor. Another manner could be the use of speckles, spots or structured light. The movement, creation or disappearance of a speckle depends on the movement of the surface vis-à-vis a detector and/or an emitter. When structured light, such as a grid or spots, is fed on to an element which moves, the pattern on the element will alter in a way in which the movement may be determined.

A controller is provided. A controller may be a single element or a combination of elements in communication with each other. A controller may be or may comprise a processor, an ASIC, an FPGA, a DSP or the like. The controller may be hardwired, or software controlled, or a combination thereof, and is configured to determine the physiological parameter from the first information and the second information. Clearly, the controller may be configured to perform additional tasks if desired.

As an example, the present system may form part of a hearing aid or hearable for positioning in or at an ear canal and for determining e.g., blood pressure, pulse, activity, or the like of a user. The controller may then also perform other controlling, such as of components of the hearable/hearing aid.

According to another example, the present system forms part of a wearable device positioned around the wrist for determining e.g., blood pressure, pulse, activity or the like of a user. The controller may then also perform other controlling, such as of components of the wearable device. In one embodiment of this example, the present system forms part of a smart device such as a smart watch.

According to yet another example, the present system is to be (removably) attached to the skin by means of a patch, an adhesive plaster. According to yet another example, the present system forms part of a patch, such as a plaster to be (removably) attached to the skin of a body that incorporates another function such as a transdermal patch or a diabetes patch, such as a diabetes patch incorporating a sensor, preferably an optical sensor, adapted for determining insulin or glucose levels in blood.

In one embodiment, the first sensor comprises a radiation source configured to emit radiation into the tissue, wherein the first sensor is configured to determine the first information based on an amount of radiation absorbed and/or scattered in the tissue. It is preferred that the radiation emitted by the first radiation source is incoherent. By using incoherent radiation, the sensor output is less sensitive to relative movement between the sensor and the tissue. Incoherent radiation may be radiation of a single wavelength or of multiple wavelengths.

A preferred type of first sensor is a PPG sensor. PPG sensors are known for determining parameters of blood and they may be made quite compact, which often is an advantage in sensors. In this context, a "PPG" measurement may relate to the amount of blood in the tissue by way of an amount of radiation absorbed thereby—by determining an amount of radiation received from the tissue and, from that radiation, an amount of radiation absorbed in the tissue.

In one embodiment, the second sensor comprises a source of coherent radiation and is capable of determining the second information based on a Doppler shift determination based on the second radiation. Doppler shifting is seen also by blood moving inside the tissue, such as when the coherent source emits radiation which is capable of travelling sufficiently far in blood perfused tissue. In this context, infrared or near infrared radiation may be suitable, such as radiation in the wavelength interval of 700-1000 nm.

Then, it may be desired that the second sensor comprises a source of coherent radiation. Alternatively or additionally, it may be desired that the first sensor comprises a source of incoherent radiation When both an incoherent and a coherent source are employed, a number of advantages are obtained, such as when the source of incoherent radiation does not emit radiation, or at least not a large amount of radiation, at the wavelength at which the source of coherent radiation emits. In this situation, the two sensors may perform their operations simultaneously even when so closely spaced that their radiation enters the same volume of the tissue and/or when the sensors are exposed to radiation from each other. In general, both sensors may emit radiation into the same volume of tissue, but the radiation from one sensor may travel further into the tissue than that from the other sensor. It may, e.g. be desired to obtain PPG/absorption information from the outermost layers of the tissue but the speed/LDV information from deeper lying portions where larger blood vessels lie.

When the second sensor comprises a source of coherent radiation, the second sensor may comprise a VCSEL with integrated photodetector. Then, if the first sensor employs a separate radiation source, such as a source of incoherent radiation, the first sensor may comprise a radiation detector separate from the source of incoherent radiation. A VCSEL (Vertical Cavity Surface-Emitting Laser) has an internal cavity in which the radiation is generated. A photodetector may be integrated into the VCSEL and which may determine a radiation intensity inside that cavity. This sensor thus is highly suitable for determining the second radiation but not the first radiation. Thus, a separate radiation detector may be provided for detecting the first radiation.

Preferably, the source of coherent radiation and the source of incoherent radiation may be operated at the same time. In this situation, the first and second radiation may be received at the same time, so that the output of the sensors will relate to the tissue in the same state, such as where the blood flow is high due to a heartbeat, where the blood vessel(s) is/are expanded, or low, such as between heart beats, where the blood vessel(s) is/are more contracted. During the time of a heartbeat period, the blood flow speed will change and the amount of blood in the tissue will change.

It may be desired to determine both the first and second information at the same time, or at least receive the first and second radiation at the same time. Alternatively, it may be desired to receive the first and second radiation at different points of time, such as points of time where the particular type of information is determined the easiest or with the highest precision.

On the other hand, such as if the radiation from one sensor disturbs the other sensor, it may be desired that the source of coherent radiation is operated within a first number of time intervals and the source of incoherent radiation is operated within a second number of time intervals, where no second time interval overlaps with any first time interval. In this manner, the sensors may be operated one at the time, so that one sensor is not disturbed by the radiation from the other. Also, this allows using a single detector for both sensors.

It may, in fact, be possible to determine which source is operating from the output of the sensors or detector(s), so that no timing is required between the operation of the sources and the determining step. For example, it may be possible to use a DC level of the output of a detector to determine which radiation source is on. In situations where two sources of radiation, such as a source of coherent radiation and a source of incoherent radiation, are used, the output intensity of these may differ to a degree where the total intensity detected from the sources differs sufficiently for the received intensity to in itself reveal which source is operating. Often, the output intensity of coherent radiation is lower than that of incoherent radiation.

Intermittent use of the radiation sources may cause a large fluctuation of the amount of light on the sensors, such as on one or more photodetectors, thus requiring a large dynamic range of any preamp(s) used. Alternatively, a preamp may be designed to be self-adaptive to the received DC signal of the photodetector, or adaptable for example by means of a DC compensation circuit comprising memory elements that preserve the required level of compensation for each cycle of the intermittent system. Additionally, the gain setting of the preamp can be designed to be self-adaptive to the received AC signal of the photodetector, or adaptable by means of a control signal that is synchronized with the intermittent drive of the light sources. Further alternatively, dual multiple preamps may be connected in parallel to the same photodetector output, each of which can be optimized for the dynamic range of the photodetector signal during operation of a corresponding light source.

It may then be desired to use the same pre-amp and/or analysis hardware, such as a processor, one or more filters, integrators, differentiators or the like, for the output of both sensors or the photodetector(s) and then provide a selector for selecting the desired sensor/detector output and the corresponding setting for DC compensation or guiding that output to the analysis hardware in sequential time intervals, such as the time intervals of operation of the respective sources.

As mentioned, it may be desired that the first sensor and the second sensor comprise and share a single detector configured to detect the first and second radiation. Alternatively, the first and second sensors may each comprise at least one detector.

Situations also exist where multiple detectors are provided and where a subset of one or more of the detectors provides an output for use only of one of the first and second information and other detector(s) provide an output used in the determination of both the first and second information.

In one embodiment, the first sensor is configured to generate a first signal based on the received first radiation, by low pass filtering the first signal and providing the first information based on the low pass filtered first signal. Typically, a low pass filtering will be configured with a corner frequency of 15-250 Hz. An alternative to the low pass filtering is to band pass filter the first signal. Typically, the bandpass filter will have a lower corner frequency from 0.01 Hz to 0.2 Hz, and a higher corner frequency of 15-250 Hz.

In the above situation or in another situation, the second sensor is configured to generate a second signal based on the received second radiation, high pass filter the second signal and provide the second information based on the high pass filtered first signal. Typically, a high pass filtering will be configured with a corner frequency of 100 Hz-20 kHz. An alternative to the high pass filtering is to band pass filter the second signal. Typically, the bandpass filter will have a lower corner frequency from 100 Hz to 20 kHz, and a suitable higher corner frequency of at most 100 kHz.

An advantage of signals relating to a speed of the blood, such as LDV or speckle contrast optical spectroscopy, over signals relating to the amount of blood in the tissue, such as PPG, is that the speed signal may be derived from interference of Doppler shifted radiation with radiation from the same coherent radiation source. For a speed signal, the blood flow speed related output signal of a photodetector is a wide-band signal, ranging from DC to more than 50 kHz. This is a much broader range than what will be experienced in a signal relating to the variation in the amount of blood in the tissue. Even artefacts caused by relative motion between the tissue and the sensor, or ambient light, will normally be in the low frequency range. Such artefacts may be created by relative motion between the sensor and the tissue, such as due to motion of the user.

Then, to obtain the second information, these lower frequencies can be rejected. This also has the advantage that the second information then is less sensitive to motion and ambient light. Also, to obtain the first information, the higher frequencies may be rejected.

In a preferred embodiment, the system comprises a source of coherent radiation and a source of incoherent radiation.

In the preferred embodiment the second sensor may be configured to have the second radiation comprise radiation from, via the tissue, the source of coherent radiation and to no substantial degree from the source of incoherent radiation.

Incoherent radiation may be suppressed or removed at the second sensor by e.g. an optical filter removing wavelengths outside of the wavelength of the coherent radiation.

In the preferred embodiment, the source of coherent radiation and the source of incoherent radiation can be configured to direct the coherent and incoherent radiation to same volume of blood perfused tissue, wherein the first sensor and the second sensor comprise one or more radiation detectors positioned to receive radiation from the volume.

According to an alternative preferred embodiment, both the first and second sensors may be configured to receive radiation from, via the tissue, a source of coherent radiation.

When the first and second information is derived from radiation from the same tissue region/volume, the first and second information can be related to each other and can be used to improve the quality of the biometric parameter.

In addition, the first and second information may be derived for the same point in time or within the same time interval again allowing a relation to exist between the first and second information.

In another embodiment of the preferred embodiment:
the source of coherent radiation may be configured to emit the coherent radiation into a first volume of the blood perfused tissue,
the source of the incoherent radiation may be configured to emit the incoherent radiation into a second volume of the blood perfused tissue, the first and second volumes being non-overlapping, and
the first sensor and the second sensor comprise one or more radiation detectors positioned to receive radiation from the first and second volumes.

When the volumes are non-overlapping, overlap or interference of the radiation from one sensor on the other may be reduced, which may simplify signal management in the system.

It may be desired that:
the first sensor comprises a first radiation source and is configured to receive the first radiation from a first volume of the tissue,
the second sensor comprises a second radiation source and is configured to receive the second radiation from a second volume of the tissue, and
the first and second sensors are configured to have:
no more than 50%, such as no more than 35%, of the first radiation stem from the second radiation source and
no more than 50%, such as no more than 35%, of the second radiation stem from the first radiation source.

This is in order to prevent cross-talk or interference of the radiation from one sensor on the other.

In this context, it may be desired that the percentage of radiation (intensity) received by one or both of the first and second sensors from the source of the other sensor is less than 25%, such as less than 20%, such as less than 10%, such as less than 5%, such as less than 1%, of the intensity received from the source of the pertaining source.

In one embodiment, the system further comprises a housing, wherein the first sensor is configured to receive the first radiation travelling in a first direction, where the second sensor is configured to receive the second radiation travelling in a second direction, and wherein the first direction is at least 90 degrees to the second direction. This housing may be configured to be provided in an ear, such as in an ear canal. Alternatively, the housing may be configured to fit around a body part, such as by providing a channel or hole in which the body part fits.

In this context, a direction may be a central direction of a field of view of the sensor. The field of view may be defined by a detector and/or one or more optical elements in front of the detector, such as one or more windows, filters, radiation guides, and/or lenses or the like.

When at least 90 degrees exist between the two directions, the volume of the tissue from which radiation may be received may be optimized. It may, however, still be possible to receive radiation from both sources, if two sources are used, even by the same detector, as radiation may travel quite far in blood perfused tissue, depending clearly on the wavelength.

The angle between the directions may be determined by projecting both directions on to a common plane, such as a plane in which at least one direction exists. The angle may be desired more than 90 degrees, such as at least 100 degrees, at least 120 degrees, at least 150 degrees or around 180 degrees. When the angle is 180 degrees, the directions may be directly opposite to each other so that if one direction is up, the other may be down.

As the detectors may reside inside the housing, the directions may penetrate the housing and thus penetrate an optical element, such as a window or a lens, forming part of the housing.

It may be desired that the first and second directions penetrate the housing at opposite surfaces of the housing.

In another embodiment, the first sensor is configured to receive the first radiation in a first field of view, and the second sensor is configured to receive the second radiation in a second field of view, wherein the first field of view and the second field of view do not substantially overlap.

In one embodiment, the controller is configured to adapt the first information based on the second information and determine the parameter from the adapted first information.

Additionally, or alternatively, the controller may be configured to adapt the second information based on the first information and determine the parameter from the adapted second information.

As described above and as elaborated on further below, the first and second information may not relate to the same parameter of the blood/tissue, but nevertheless, an overlap is seen, and contents of one of the first and second information may be used for improving the other of the first and second information.

For example, even when the volume of blood entering the tissue with a heartbeat is the same, the tissue may expand differently depending on the distensibility of the blood vessels. When the distensibility is lower, the expansion is lower and so is the amount of blood in the tissue. However, when the distensibility is lower, the speed of the blood is higher in order to transport the same amount blood through the blood vessels. Thus, the amount of blood is correlated with the speed of the blood. Then, the first information and the second information are correlated, and one may be used for enhancing or improving the other. It may be desired to correlate the part of the first information where the amount of blood is the highest with the part of the second information where the speed peaks.

In one embodiment, the controller is configured to determine the blood parameter from an equation or model comprising the first information and the second information as well as one or more calculated parameters. The parameters may be obtained from a calibration or the like. Naturally, the tissue being organic material, a variation thereof is seen both during shorter and longer time spans. Thus, it may be desired to have the parameters re-calculated and/or re-calibrated from time to time.

In one situation, the first information and/or the second information represents a periodic signal, where the controller is configured to calculate the parameters from the first information and/or the second information for a period of time being at least a period of the periodic signal. The period of time may be at least a period of the pulse, i.e. at least one heartbeat.

The parameter may be calculated using, for example, a least mean square method.

Naturally, the calculation or recalculation of the parameters may be performed regularly, intermittently or the like, such as for each heartbeat, every X heart beats, every X minutes or hours or days, if desired. Alternatively, the parameters may be recalculated if the output of the determining step varies in an undesired manner, falls outside of predetermined limits or the like.

As mentioned above, the parameter may be heartrate, heart rate variability, breathing rate, peripheral oxygen saturation ($SpO_2$), blood perfusion of the tissue, blood flow speed, blood pressure, arterial distensibility, user motion detection, or user activity detection.

In a particularly relevant embodiment:
the first sensor comprises a first emitter configured to emit first radiation into the blood-perfused tissue;
the second sensor comprises a second emitter configured to emit second, coherent, radiation into the blood-perfused tissue;
the first and second sensors comprise at least one radiation detector configured to detect:
scattered radiation from the blood-perfused tissue emitted by the second emitter and
scattered radiation from the blood-perfused tissue emitted by the first emitter;
the second sensor is configured to derive the second information based on a doppler shift in the scattered radiation,
the first sensor is configured to derive the first information from intensity variation in the scattered radiation;
the controller is configured to
either:
calculate a first calculated signal from the second information and/or calculate a second calculated signal from the first information;
use the first calculated signal and the first information to calculate an improved first information and/or use the second calculated signal and the second information to calculate an improved second information; and
determine the physiological parameter from the improved first information and/or improved second information;
or:
calculate a synthetic time derivative of the first information from the second information and the first information; and
determine physiological parameter from the synthetic time derivative of the first information.

Thus, the first radiation may be coherent or not, preferably incoherent.

The first and second sensors may share one or more detectors or separate detectors may be employed, such as when using the VCSEL with integrated photodiode as described above.

The first and second information are provided or obtained but one or both are improved using the other. The first information may be improved by calculating the calculated first signal from the second information. This calculated first signal may then be used for improving the first information to arrive at improved first information. The improvement may be any type of improvement, such as an improvement in signal to noise ratio, a lowered measuring/calculating uncertainty, or the like, of the (improved) first information and/or the actual parameter determined based thereon.

Naturally, the same may be performed on the second information, and both the first and second information may be improved and used in the determination of the parameter.

In general, the operation of the controller may be split up into elements or blocks. The determination of the improved first/second information may be handled by one block and the determination of the parameter by another block or another controller altogether. In fact, the same controller may be used also for determining the first and second information, so that the controller may perform part of the operation of the sensors, Depending on the type of the first/second information. If the first/second information is more complex information, such as a value, this may be determined in the controller and not necessarily of a piece of hardware particular to that sensor.

In general, the second emitter may be configured to emit second coherent radiation having a wavelength in the near infra-red spectrum or infra-red spectrum, preferably the near infra-red spectrum. Preferably, this radiation is coherent.

Typically, the first emitter may be configured to emit first radiation having a wavelength in the range of from 450 to 1000 nm. Preferably, the first emitter is configured to emit a first radiation that is essentially monochrome.

The system of present invention, whilst in use, may be completely operated from the same part of the body where the sensors of the system are operating. In some embodiments, it may be desired to use an apparatus that incorporates a first and a second sensor and a communication means to communicate with the controller, typically located remotely from the apparatus. It may also be desired that the apparatus incorporates part of the function performed by the controller to be used in the system of the invention, such as signal processing or a part thereof and communication means to communicate data from such (part) signal processing to a controller performing the other functions of the system of the invention.

In general, it may be desired that the apparatus comprises at least two radiation detectors wherein a second radiation detector is configured to detect second scattered radiation from blood-perfused tissue radiated by the second coherent radiation and a first radiation detector is configured to detect first scattered radiation from blood-perfused tissue radiated by the first radiation.

Then, the second sensor may be a laser Doppler velocimetry (LDV) detector and/or the first sensor may be a photoplethysmography (PPG) detector. Specifically, an LDV detector is currently preferred over a speckle contrast sensor, as no image processing is required for LDV. Particularly, the computational requirements for processing LDV signals are lower than for processing speckle contrast sensor, whereas the measurement quality is similar.

In general, the signal processor may be configured to calculate a first calculated signal from a second information and add the first calculated signal to the first information to calculate an improved first information, having an improved signal to noise ratio relative to the first information.

According to a second aspect of the invention, in one embodiment, the apparatus, as described in any of the above embodiments, comprises:

a first sensor configured to emit first radiation into blood-perfused tissue of the body;

a second sensor configured to emit second, coherent, radiation into blood-perfused tissue of the body, where the first and second sensors comprising at least one radiation detector configured to detect scattered radiation from the blood-perfused tissue radiated by the first radiation and/or the second coherent radiation; and a communication means configured for communicating information relating to the scattered radiation to a signal processor configured to derive a first signal from intensity variation in the scattered radiation and a second signal from a doppler shift in the scattered radiation.

In another embodiment, an apparatus for use in a system according to any one of the above embodiments, may comprise:

a first sensor configured to emit first radiation into blood-perfused tissue of the body;

a second sensor configured to emit second, coherent, radiation into blood-perfused tissue of the body, where the first and second sensors comprise at least one radiation detector configured to detect scattered radiation from blood-perfused tissue radiated by the first radiation and/or the second coherent radiation;

a signal processor configured to derive a first signal from intensity variation in the scattered radiation and a second signal from a doppler shift in the scattered radiation; and a communication means configured for communicating the first signal and the second signal to a signal processor configured to calculate a first calculated signal from a second signal and/or calculate a second calculated signal from a first signal and use the first calculated signal and the first signal to calculate an improved first signal and/or use the second calculated signal and the second signal to calculate an improved second signal; or a communication means configured for communicating the first signal and the second signal to a signal processor configured to calculate a synthetic time derivative of the first signal from the first and second signal.

In one embodiment, an apparatus for use in a system according to any one of the preceding embodiments, comprises:

a second sensor configured to emit second, coherent, radiation into blood-perfused tissue of the body;

a first sensor configured to emit first radiation into blood-perfused tissue of the body, where the first and second sensors comprise at least one radiation detector configured to detect scattered radiation from blood-perfused tissue radiated by the second coherent radiation and/or the first radiation;

a signal processor configured to derive a first signal from intensity variation in the scattered radiation and a second signal from a doppler shift in the scattered radiation; to calculate a first calculated signal from the second signal and/or calculate a second calculated signal from the first signal and use the first calculated signal and the first signal to calculate an improved first signal and/or use the second calculated signal and the second signal to calculate an improved second signal, or calculate a synthetic time derivative of the first signal from the first and second signal; and communication means configured for communicating the improved first signal and/or the improved second signal or the synthetic time derivative of the first signal and the first signal, to a controller configured to determine the physiological parameter from the improved first signal and/or improved second signal or the synthetic time derivative of the first signal and the first signal.

Naturally, the above apparatus or systems may form part of a wearable, such as a hearing aid, a hearable, a watch, a patch, an earbud or the like. Further, all embodiments, situations, considerations, and definitions made in relation to the first aspect are equally relevant for the second aspect of the invention to the extent the apparatus to be used in the system incorporates the relevant functions.

A third aspect of the invention relates to a method of determining a physiological parameter of a body comprising blood perfused tissue, the method comprising:

providing first information from a first sensor receiving
first radiation from the blood perfused tissue, the first
information relating to an amount of blood in the tissue,
providing second information from a second sensor
receiving second radiation from the blood perfused
tissue, the second information relating to a speed of
blood in the tissue,
determining the physiological parameter from the first
information and the second information.

According to one embodiment, the method comprises
determining the physiological parameter by:
calculating a first calculated signal from the second infor-
mation and/or calculating a second calculated signal
from the first information;
using the first calculated signal and the first information to
calculate an improved first information and/or using the
second calculated signal and the second information to
calculate an improved second information; and
determining the physiological parameter from the
improved first information and/or improved second
information.

According to another embodiment the method comprises
determining the physiological parameter by:
calculating a synthetic time derivative of the first infor-
mation from the second information and the first infor-
mation; and
determining the physiological parameter from the syn-
thetic time derivative of the first information.

In this embodiment, the physiological parameter is pref-
erably determined from the synthetic time derivative of the
first information and the first information, preferably using
a first or second order Windkessel model.

Naturally, all embodiments, situations, considerations,
and definitions made in relation to the first aspect are equally
relevant for the third aspect of the invention.

Thus, the parameter and the blood perfused tissue may be
as described above.

The method comprises providing first information from a
first sensor receiving first radiation from the blood perfused
tissue. The first information may be as described above. The
first radiation may be generated by the blood and/or tissue,
such as by fluorescence, radiation or emission, it may be
scattered/reflected by the blood and/or tissue or it may be
transmitted through the blood and/or tissue.

The first and second sensors may be as described above.

The first information relates to, as in the first aspect, an
amount of blood in the tissue. This amount may be deter-
mined from the amount of first radiation received, scattered,
absorbed or the like. The intensity of the first radiation may
indicate the amount of blood. A higher intensity may indi-
cate a higher amount of blood, if the first radiation is e.g.
emitted by the blood. A lower intensity may indicate a higher
amount of blood if the first radiation is absorbed by the
blood and the first radiation is e.g. a non-absorbed portion of
radiation launched into the tissue.

The method also comprises providing second information
from a second sensor receiving second radiation from the
blood perfused tissue, where the second information relates
to a speed of blood in the tissue. As mentioned above, the
speed may be determined from the second radiation if this
radiation is Doppler shifted by constituents of the moving
blood.

The parameter may be determined as described above.
This determination may be made in a controller or processor
if desired. The parameter may be output, illustrated, indi-
cated, interpreted or the like to a person, operator, or health
professional.

In one embodiment, the step of proving the first informa-
tion comprises:
controlling a radiation emitter to emit, preferably inco-
herent, radiation into the tissue and
determining the first information based on an amount of
the radiation absorbed and/or scattered in the tissue.

As mentioned, absorption but also scattering may depend
on the amount of blood in the tissue so that the first
information may be derived from the intensity variation of
the received signal.

In that embodiment, the step of providing the first infor-
mation may comprise providing PPG information.

In that or another embodiment, the step of providing the
second information comprises:
controlling a source of coherent radiation to emit coherent
radiation into the tissue and
determining the second information based on a Doppler
velocity or Doppler shift determination based on the
second radiation.

When the second radiation is a Doppler shifted version of
the coherent radiation, the relative movement of the scat-
tering portions of the blood, typically blood cells, may be
determined.

In a preferred embodiment, the second sensor and the first
sensor output coherent radiation and incoherent radiation.
When the radiation is output by the sensors, radiation is not
required generated and emitted by the blood or tissue, which
would be possible if the blood comprises a radiating or
fluorescing agent.

When the first and second sensors output the coherent and
incoherent radiation:
1. the second sensor may comprise a VCSEL with inte-
grated photodetector and the first sensor may comprise
a radiation detector separate from the integrated pho-
todetector,
2. the coherent radiation and the incoherent radiation may
be emitted at the same time,
3. the coherent radiation may be emitted within a first
number of time interval and the incoherent radiation
may be emitted within a second number of time inter-
vals, where no second time interval overlaps with any
first time interval, and/or
4. the determining step may comprise a single detector
detecting the first and second radiation.

In relation to option 1, the integrated photodetector is
highly suitable for determining the second radiation but not
necessarily the first radiation. Thus, a separate radiation
detector may be provided for detecting the first radiation.

In relation to option 2, when the coherent and incoherent
radiation is emitted at the same time, the resulting first and
second radiation will be received from the tissue at the same
time. This has the advantage that the first and second
information is derived from the tissue with the same con-
dition, such as with the same amount of blood, the same
expansion or contraction of the blood vessels, but also with
the same relative position and/or motion between the
sensor(s) and the tissue. Thus, temporal and spatial variance
may then not affect the accuracy of the parameter extraction, In relation to option 3, the coherent and incoherent
radiation is output in non-overlapping time intervals so that
the first and second radiation may be received at different
points in time or within different time intervals. In this
context it is noted that the sensors may both receive radiation
simultaneously, i.e. radiation stemming from either the
coherent or the incoherent radiation, but the sensors or the
controller may be capable of determining whether which
sensor output is to be used for the first or the second information. It may be desired to ignore the output of one sensor during one time interval, or when the coherent radiation is emitted, and ignore the output of the other sensor when the incoherent radiation is emitted.

In relation to option 4, a single detector may be used for generating the first and second information, especially during option 3 where the coherent and incoherent radiation is not emitted simultaneously. Then, the output of the detector may be used for the first and second information during the pertaining, non-overlapping, time intervals.

Also, or alternatively, in the preferred embodiment:
the first radiation comprises radiation from, typically via the blood/tissue, the incoherent radiation and
the second radiation comprises radiation from, typically via the blood/tissue, the coherent radiation and to no substantial degree any of the incoherent radiation.

Naturally, undesired radiation may be prevented from reaching a sensor or detector by an optical filter, such as if the other source does not emit, or at least not solely, radiation at the wavelength removed by the filter.

Often, the output intensity of coherent radiation is of a lower intensity than coherent radiation, so that the intensity of received coherent radiation may not interfere with the received incoherent radiation. Also, or alternatively, such as if the first radiation relates to an absorbed amount of radiation, the coherent radiation may also be absorbed and thus used in the same manner as the incoherent radiation.

On the other hand, the incoherent radiation may interfere with the second sensor in the situation where the second sensor operates on the Doppler effect. Then, the original radiation may be compared to the received radiation to determine a phase shift and from that a speed. This phase shift determination may be polluted by noise caused by the incoherent radiation. Then, this incoherent radiation may be desired removed or attenuated at the second sensor.

In the preferred embodiment, the coherent radiation and the incoherent radiation may be directed to same volume of blood perfused tissue, wherein the first sensor and the second sensor comprise one or more radiation detectors positioned to receive radiation from the volume.

When the first and second radiation is received from the same volume of tissue, the first and second information may be more easily correlated.

In the preferred embodiment it may be desired that:
the coherent radiation is emitted into a first volume of the blood perfused tissue,
the incoherent radiation is emitted into a second volume of the blood perfused tissue, the first and second volumes being non-overlapping, and
the first sensor and the second sensor comprise one or more radiation detectors positioned to receive radiation from the first and second volumes.

Thus, the radiation is emitted into non-overlapping volumes.

In general, it is noted that the radiation may travel far into the tissue and also be scattered into new directions, so that radiation launched into one area may find its way into the other area. A radiation source has a field of view, defined by the source or optics in front of it, into which the radiation is launched.

The radiation launched in the field of view usually will have an intensity distribution from a central or main direction of the radiation, such as a direction along which the largest intensity is emitted, and in a direction therefrom, often perpendicular to the main direction. The field of view may be defined as the directions at which the intensity emitted is 10% or more, such as 25% or more, such as 50% or more of the intensity output along the direction having the maximum intensity.

Also, the radiation may be attenuated, such as scattered or absorbed, in the tissue, so that the intensity drops with the distance travelled in the tissue. Then, the volume may be determined as that within a predetermined distance from a surface thereof receiving the radiation. This distance may be 1-20 mm, such as 2-10 mm. Additionally or alternatively, the distance may be determined as one where the radiation intensity, such as at a predetermined wavelength, has been attenuated 25%, such as 50%, such as 75%.

The volume may be determined as a combination of the field-of-view considerations and the distance considerations.

A field of view of a detector may be defined in the same manner, as the detector will have a field of view with a varying detection efficiency over the field of view. Thus, the field of view may be defined by the detector or optics in front of it, which may be defined by a minimum detection efficiency. Also, a volume may be determined by that field of view and a depth determined as a distance or a distance related to an absorption of the radiation.

In one embodiment, the step of providing the first information comprises generating a first signal based on the received first radiation and low pass filtering the first signal. Alternatively, the first signal may be band pass filtered. As described above, the first signal relates to the amount of blood and may relate to relatively slowly varying parameters compared to the second information relating to the speed of the blood. This speed varies, depending on which blood vessels penetrate the tissue, rather step variations. Naturally, the speed of the blood in arteries close to the heart will be much higher than the speed in arteries far from the heart— and in veins.

In that or another embodiment, the step of providing the second information comprises generating a second signal based on the received second radiation and high pass filtering, or alternatively band pass filtering, the second signal. As explained above, the second information will often relate to higher frequency information than the first information, so these signals may be separated by a simple filtering.

In one embodiment:
the step providing the first information comprises operating a first sensor to receive the first radiation from a first volume of the tissue,
the step of proving the second information comprises operating a second sensor to receive the second radiation from a second volume of the tissue, and
the first and second sensors have:
no more than 50%, such as no more than 35%, such as no more than 25%, such as no more than 15%, such as no more than 5%, such as no more than 1%, of the first radiation stemming from the second radiation source and
no more than 50%, such as no more than 35%, such as no more than 25%, such as no more than 15%, such as no more than 5%, such as no more than 1%, of the second radiation stemming from the first radiation source.

In this embodiment, the volumes may be overlapping or not and may be defined in any desired manner.

A limit is then desired to the amount of radiation, at one sensor, stemming from the other sensor. Radiation from the two sensors may be different, such as exemplified further above where one sensor emits coherent radiation and the other incoherent radiation. The difference may also stem from the sensors emitting radiation at different wavelengths or radiation within different, overlapping or non-overlapping, wavelength intervals.

In one embodiment:

the step of providing the first information comprises receiving the first radiation where the first radiation travels in a first direction, the step of providing the second information comprises receiving the second radiation where the second radiation travels in a second direction, and wherein the first direction is at least 90 degrees, such as at least 120 degrees, such as at least 150 degrees, to the second direction.

In this connection, the direction of the radiation may be a direction along which the pertaining sensor is the most sensitive. A sensor has a field of view and often has a direction along which it is the most sensitive. Alternatively, the direction may be an axis of symmetry of the sensor.

The angle may be determined in the plane described above.

When the directions are at least 90 degrees to each other, interference at one sensor by radiation from the other sensor may be naturally limited.

In a preferred situation, the first and second radiation penetrate the housing at opposite surfaces of the housing, where "opposite" may mean that the angle between the directions, in the plane, is at least 170 degrees.

As mentioned above and elaborated on below, the first and second information may be correlated. For example, when the blood speed is high, the blood vessels are expanded so that the amount of blood in the tissue is increased. This correlation may be used for improving the information. Thus, in one embodiment, the determining step comprises adapting the first information based on the second information and determining the parameter from the adapted first information. In that or another situation, the determining step comprises adapting the second information based on the PPG information and determining the parameter from the adapted second information.

In one embodiment, the parameter is heartrate, heart rate variability, breathing rate, peripheral oxygen saturation ($SpO_2$), blood perfusion of the tissue, blood flow speed, blood pressure, arterial distensibility, user motion detection, or user activity detection.

As is also indicated above, in one embodiment, the determining step comprises determining the blood parameter from an equation comprising the first information and the second information as well as one or more calculated parameters. Then, the first information and/or the second information represents a periodic signal and where the calculated parameters are calculated from the first information and/or the second information for a period of time being at least a period of the periodic signal.

In a particularly interesting embodiment:

the step of providing the first information comprises a first emitter of the first sensor emitting first radiation into the blood-perfused tissue;

the step of providing the second information comprises a second emitter of the second sensor emitting a second, coherent, radiation into the blood-perfused tissue;

the steps of providing the first and second information comprise detecting:

scattered radiation from the blood-perfused tissue emitted by the second emitter and scattered radiation from the blood-perfused tissue emitted by the first emitter;

the step of providing the second information comprises deriving the second information based on a doppler shift in the scattered radiation, the step of providing the first information comprises deriving the first information from intensity variation in the scattered radiation;

the step of determining the parameter comprises:

calculating a first calculated signal from the second information and/or calculating a second calculated signal from the first information;

using the first calculated signal and the first information to calculate an improved first information and/or using the second calculated signal and the second information to calculate an improved second information; and determining the physiological parameter from the improved first information and/or improved second information.

As mentioned above, the improved information may be improved in a number of ways, such as by having a higher confidence, a lower noise, or the like.

As described above, the physiological parameter is determined from first information relating to an amount of blood in the tissue and second information relating a speed of blood in the tissue. Generally, the first and second information are provided in the form of signals generated by the first sensor and the second sensor, respectively. The signal generated by the sensors typically comprises a series of pulses (also referred to as waveforms), with each pulse corresponding to the signal during one heartbeat period. Advantageously, the first and second signal are subdivided into individual pulses by the system, e.g. by the sensors or, preferably, by the controller.

For example, the system (e.g. the controller) is configured to determine triggers for the first and second signals to define fractions thereof. Preferably, the triggers define a signal fraction that corresponds with a full period of a heartbeat. Many signal processing methods are known for extracting a single heartbeat period from a physiological signal, and the invention is not limited to a specific one of these methods. A non-exhaustive list of examples for determining the two triggers for the first and/or second signal include: determining time points of rising edges of the signal; determining time points where the signal has a maximum; determining time points where a derivative of the signal has a maximum, determining a zero-crossing of the signal, determining a zero-crossing of the derivative of the signal, determining the time points that an integral of the signal crosses a threshold.

In the context of the invention, the processing of the first and second information may be performed on single signal fractions or on multiple signal fractions, such as multiple consecutive signal fractions. In a particular example, an ensemble average of a predetermined number of signal fractions is computed, and the processing is performed using the ensemble average. The ensemble average is for example computed by adding a predetermined number N of signal fractions, and dividing by N. The ensemble average is for example computed as a moving average, a weighted moving average or an exponential moving average. In particular, more recent signal fractions may be assigned a greater weight than older signal fractions.

In a first example, a first (resp. second) calculated signal is calculated from an ensemble average of N signal fractions of the second (resp. first) information. The improved first (resp. second) information is calculated using the first (resp. second) calculated information and the ensemble average of the first (resp. second) information. The physiological parameters is determined from the improved first information and/or improved second information.

In a second example, a synthetic time derivative is computed from a first ensemble average, computed from N signal fractions of the first information, and a second ensemble average, computed from M signal fractions of the second information. N and M can be chosen differently or, preferably, equal (N=M). The physiological parameter is determined from the thus calculated synthetic time derivative and, optionally, the first ensemble average.

According to a further aspect, a computer program is provided that comprises instructions which, when executed by a computing device or system, cause the computing device or system to perform the method according to any of the embodiments described herein. In a further aspect, the invention comprises a computer-readable medium storing said computer program. Preferably, the computer program comprises instructions which, when executed by a computing device or system, cause said computing device or system to execute the steps of: obtaining first information relating to an amount of blood in the tissue from a first sensor receiving first radiation from the blood perfused tissue, and obtaining second information relating to a speed of blood in the tissue from a second sensor receiving second radiation from the blood perfused tissue. For example, the first and second information are obtained as data via wired or wireless connections between the computing device or system and the first and second sensors, respectively. According to a first aspect, the instructions include instructions to execute the steps of: calculating a first calculated signal from the second information using a model that predicts first information relating to an amount of blood in the tissue from second information relating to a speed of blood in the tissue and/or calculating a second calculated signal from the first information using a model that predicts second information relating to a speed of blood in the tissue from first information relating to an amount of blood in the tissue; using the first calculated signal and the first information to calculate an improved first information and/or using the second calculated signal and the second information to calculate an improved second information; and determining the physiological parameter from the improved first information and/or improved second information. According to a second aspect, the instructions include instructions to execute the step of determining the physiological parameter by: calculating a synthetic time derivative of the first information from the second information and the first information; and determining the physiological parameter from the synthetic time derivative of the first information.

BRIEF DESCRIPTION OF THE DRAWINGS

In the following, preferred embodiments will be described with reference to the drawings, wherein:

FIG. 6, FIG. 9 illustrates a fourth embodiment of illustrates another embodiment of front-end signal processing, the device or system according to the invention.

DETAILED DESCRIPTION

Figure 1:
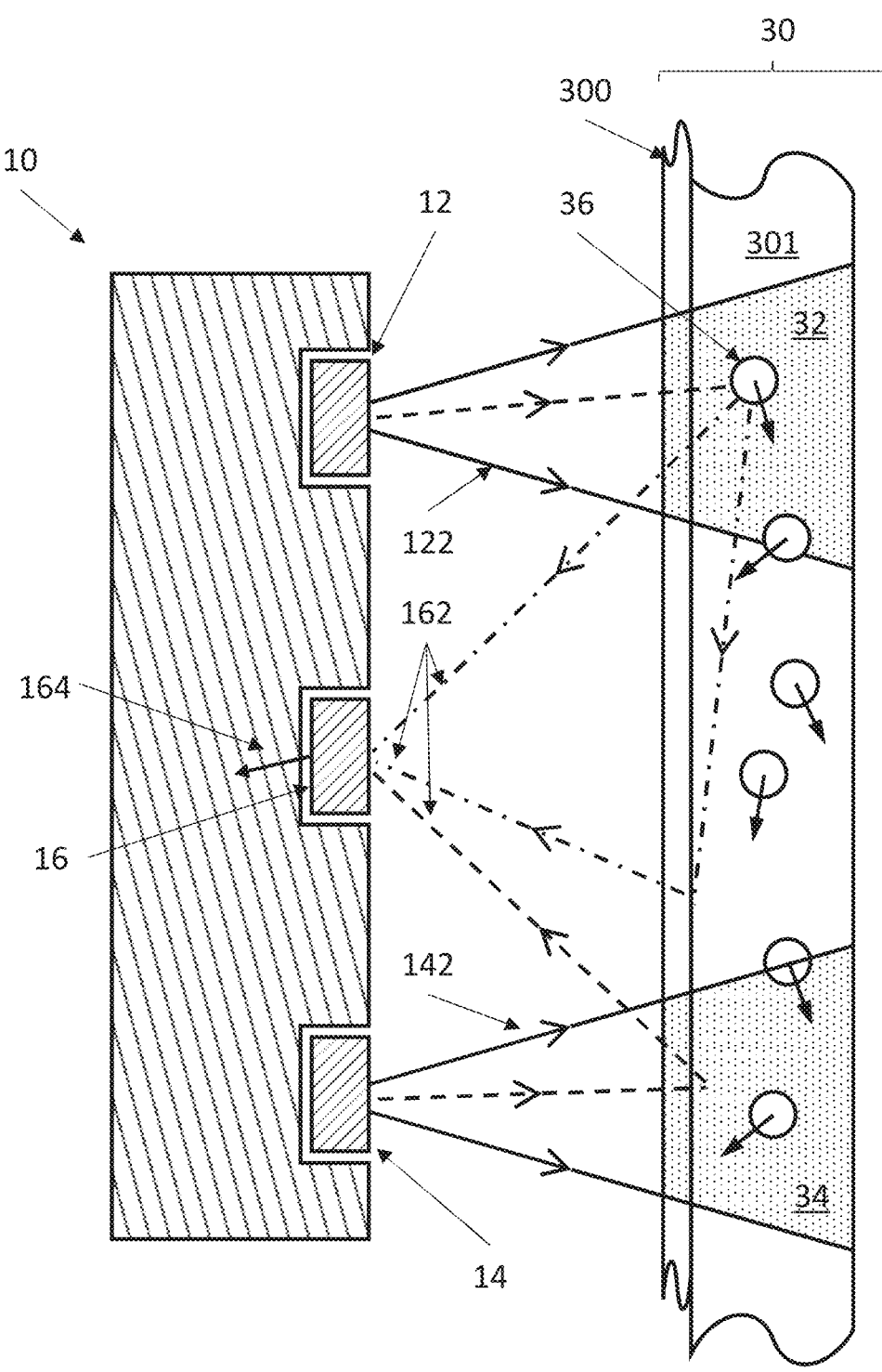
FIG. 1 illustrates a first embodiment of the device or system according to the invention.

A first embodiment of the invention is depicted in FIG. 1. FIG. 1 shows a cross section view of a body-worn device or system 10 and a cross-sectional view of a region of blood perfused tissue 30. The device 10 comprises a coherent radiation source 12 (e.g. laser, VCSEL) and an incoherent radiation source 14 (e.g. LED), radiation (122 and 142) from both exposing and penetrating the skin 300 and other parts of the tissue 30 into exposed tissue regions 32 and 34, respectively. In this embodiment, the exposed tissue regions 32 and 34 do not coincide, but this is not essential, and for some biometric parameters it can be advantageous that the exposed regions coincide as much as possible.

Discontinuities of optical properties in the tissue 30 can scatter the radiation in other directions than that of the incident direction, and moving discontinuities 36, e.g. blood cells, moving in blood vessels 301 can Doppler-shift as well as scatter the radiation. A photodetector 16 receives (162) correlated Doppler-shifted and scattered radiation and uncorrelated scattered radiation (and also Doppler-shifted incoherent radiation).

The general amount of radiation absorbed in the tissue 30 may relate to the amount of blood therein, as the absorption of the blood reduces the amount of scattered light, and may be represented by first information, and the Doppler shifting will relate to a blood speed and may be represented by second information. All this information may be derived from the output signal 164 of the detector 16.

Thus, the device 10 may be seen as comprising two sensors, a sensor measuring the radiation from the source 12 and a sensor measuring the radiation from the source 14, where the two sensors share the detector 16. The deriving of the signals from these sensors will be described further below.

For example, the low-frequency component of the output signal of the photodetector 16 is proportional to the total amount of radiation, while the high-frequency component contains contributions caused by the interference of the Doppler-shifted and non-shifted coherent radiation.

Figure 2:
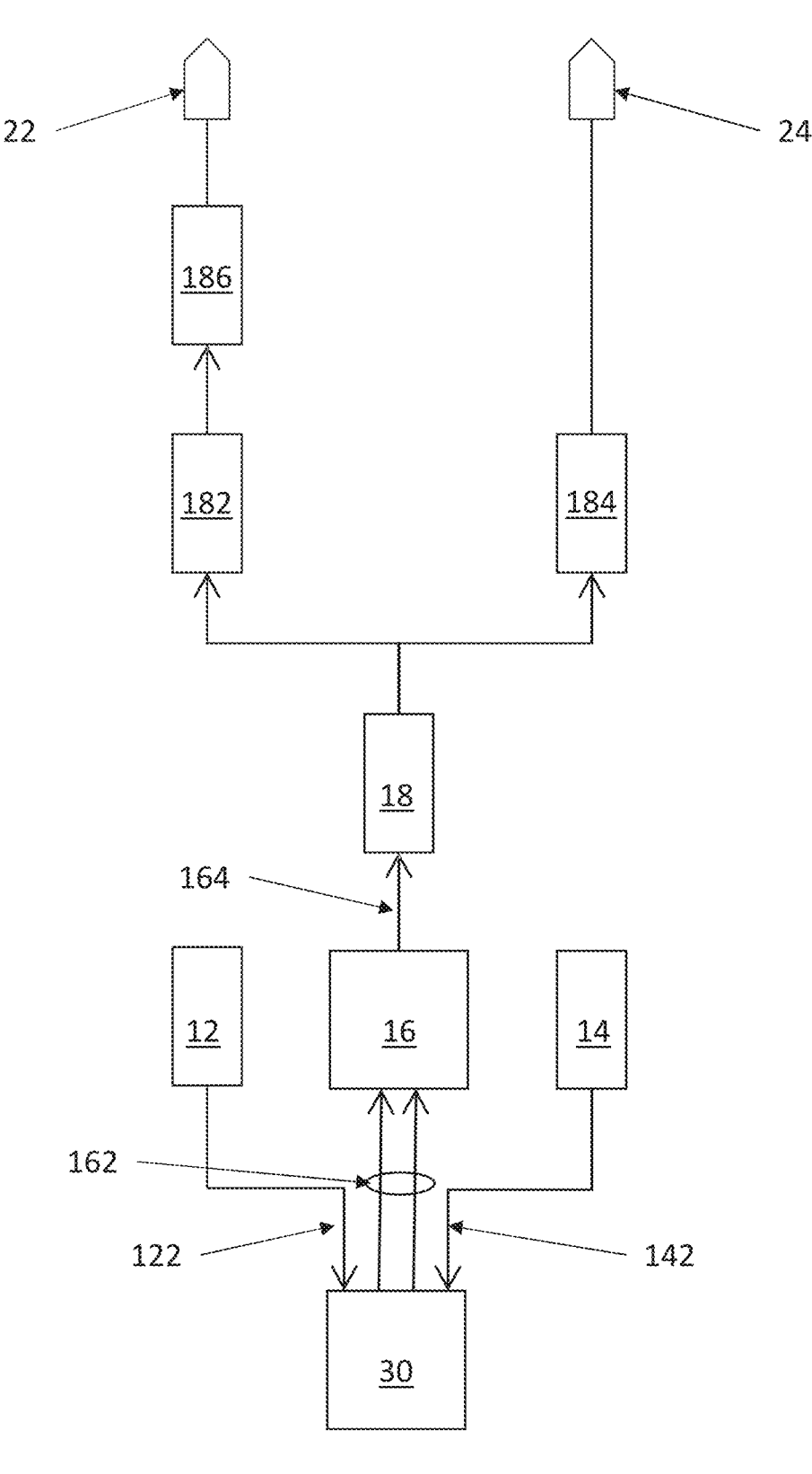
FIG. 2 illustrates an example of a front-end signal processing for a device according to the invention.

FIG. 2 shows a block diagram of the front-end signal processing for the device of FIG. 1. The main purpose of the front-end signal processing is to derive a first information 24, relating to the blood amount or volume, and a second information 22, relating to the blood speed, from the photodetector output 164. Different approaches are possible for this. The first is depicted in FIG. 2 and can be applied if both radiation sources 12 and 14 are operating continuously, and the front-end signal processing uses known frequency ranges of both signals. Preferably, pre-amp 18 is provided, as the output signals from the detector 16 is usually quite weak. The first signal, or the first information 24, is extracted from the photodetector output 164 (optionally amplified by pre-amp 18) by means of a low-pass filter 184, which may be embodied as a bandpass when, as preferred, DC is not desired and thus blocked or filtered-out. The second signal, or the second information 22, is extracted from the photo-detector output 164 (optionally amplified by pre-amp 18) by means of a high-pass filter 182, which may be embodied as a bandpass if very high frequencies, often containing only noise, are undesired and thus suppressed.

From the second signal or information 22, the average Doppler-shift may be obtained from the wide-band like signal by means of calculating the $1^{st}$ moment, in the element 186, of the spectrum:

$$M_1(t) = \int_{f1}^{f2} f \cdot S_v(f, t)\, df$$

where:

M₁(t) is the first moment of the spectral density at time t,
f₁ and f₂ are the limits of the band pass filter, and
s_v(f,t) is the spectral amplitude density of the photode-tector output.

The magnitude of the first moment is proportional to the average Doppler shift of the radiation received by the photodetector and proportional to the intensity of the radiation. The first moment may be normalized in order to remove or reduce the dependency of the intensity by dividing it by the average determined over the same frequency band.

$$v(t) = \frac{M_1(t)}{M_0(t)}$$

wherein:

v(t) is the average Doppler shift at time t,
M₀(t) is the average spectral density at time t.

Figure 3:
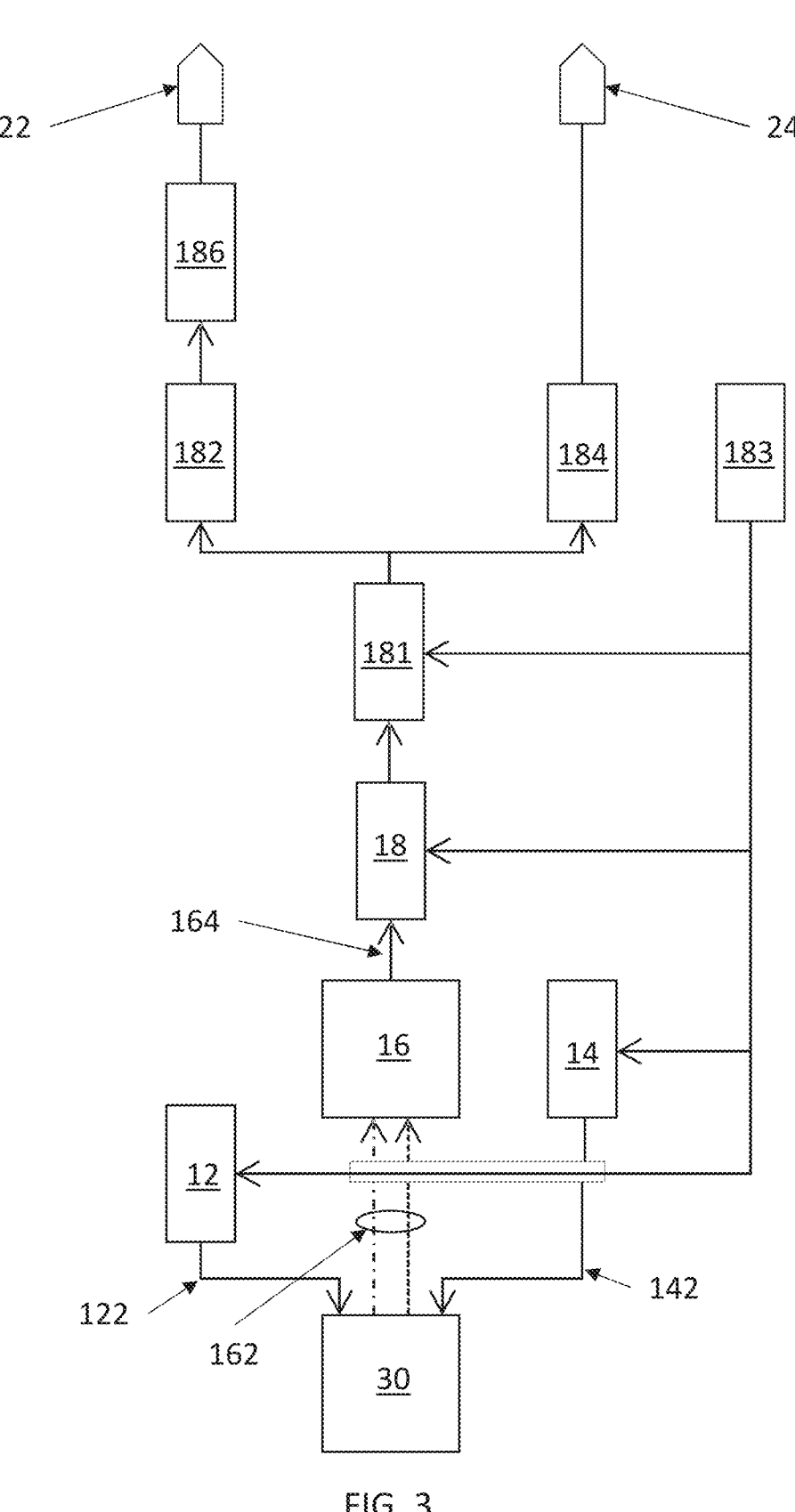
FIG. 3 illustrates another example of a front-end signal processing for a device according to the invention.

FIG. 3 shows another example of a block diagram for a signal processing of the set-up seen in FIG. 1 and which can be applied if at least one of the sources is operating inter-mittently.

The extraction of the first and second signals/information 22/24 from the photodetector output 164 can be performed by time-windowing of the signal processing after the preamp 18. If the output signals of the preamp 18 are digitized, this digitization should also be performed with the same timing.

In FIG. 3, a selector 181 is seen which is capable of routing the output of the preamp 18 to either of the filters 182 and 184. The selector 181 is controlled by a timing circuit 183 which also operates the sources 12/14 to achieve the intermittent operation. The timing circuit 183 operates source 12 while instructing the selector 181 to forward the output of the preamp 18 to the filter 182 for generation of the second signal or information 22. At a later point in time, the timing circuit 183 will instead operate source 14 while instructing the selector 181 to forward the output of the preamp 18 to the filter 184 for the generation of the first information or signal 24.

As is known, intermittent use of the radiation sources 12/14 may cause a large fluctuation of the amount of radiation on the photodetector. This may be managed in a number of ways. In one embodiment, a preamp 18 is used having a large dynamic range. Alternatively, the preamp 18 may be designed to be self-adaptive to the received DC signal of the photodetector 16, or adaptable for example by means of a DC compensation circuit comprising memory elements that preserve the required level of compensation for each cycle of the intermittent system.

Additionally, the gain setting of the preamp 18 can be designed to be self-adaptive to the received AC signal of the photodetector 16, or adaptable by means of a control signal that is synchronized with the intermittent drive of the radiation sources 12/14. Another alternative can be to have multiple preamps 18 connected in parallel to the same photodetector output, each of which can be optimized for the dynamic range of the photodetector signal during operation of a corresponding radiation source.

Instead of using the timing circuit 183, a DC level of the photodetector 16 may be used in order to detect which radiation source 12/14 is active (at least in case the DC is different between operation of the two radiation sources 12/14) and can be used to select the signal processing channel 184 or 182+186, such as using the selector 181, and/or select the setting for DC compensation and/or select the gain setting of the preamp 18 corresponding to the active radiation source 12/14.

Intermittent operation of the radiation sources 12/14 may be advantageous in case a continuous operation thereof would consume too much current from e.g. a battery of the body-worn device 10.

Figure 4:
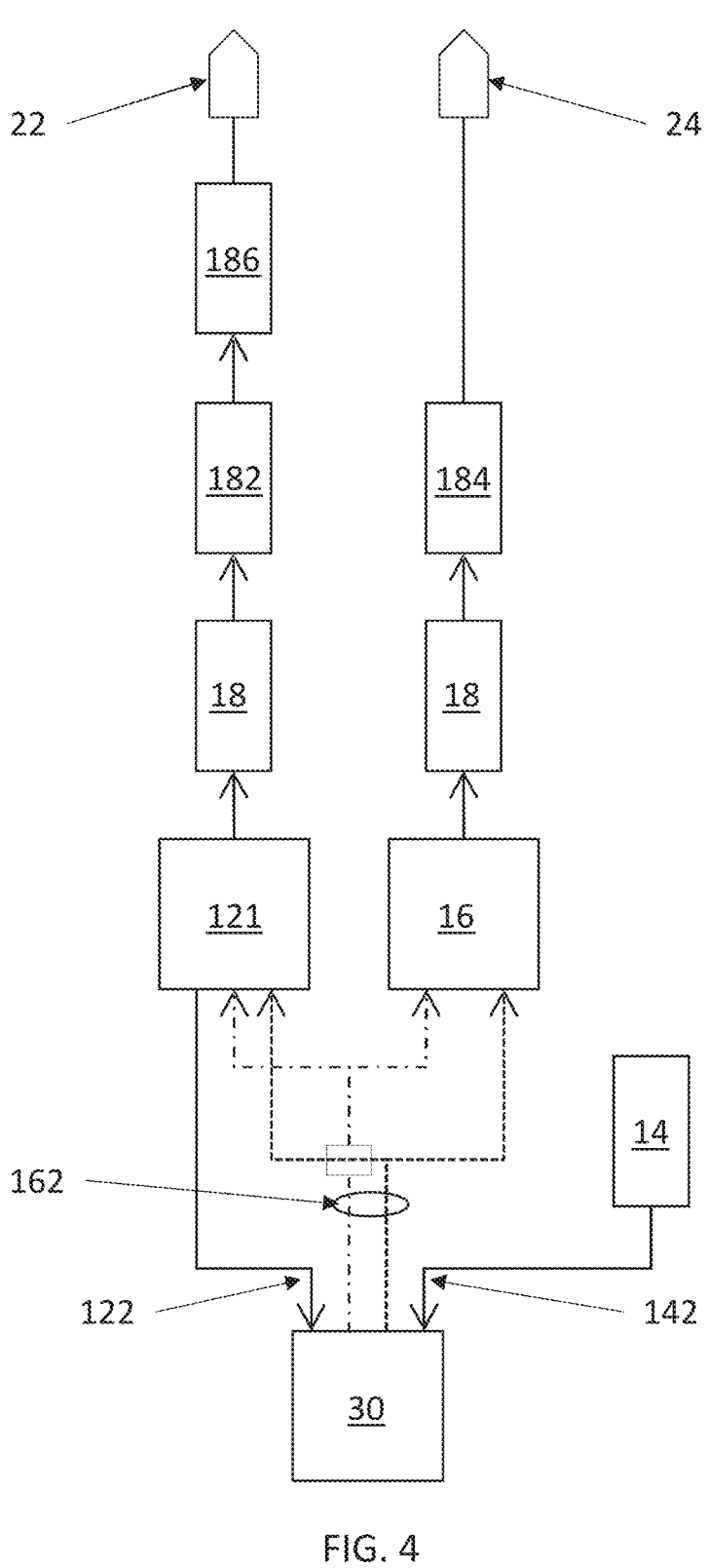
FIG. 4 illustrates yet another example of a front-end signal processing for a device according to the invention.

FIG. 4 depicts another block diagram for the signal processing, which can be applied if the coherent radiation source 12 comprises a separate detector, such as an inte-grated detector, forming element 121, such as if it is a VCSEL with integrated photodetector. In general, the coher-ent radiation from the emitter will be fed to the detector both via and not via the tissue in order for the radiation to interfere (self-mix) and thus create the Doppler information. When the element 121 is a VCSEL with Integrated Photo-detector, the detector is positioned to detect radiation inside the actual laser cavity. Self-mixing will thus take place in the cavity of the VCSEL. When positioned inside the cavity, any incoherent radiation entering the cavity does not interfere with the coherent radiation therein. This incoherent radiation then will only affect the DC level of the photodetector. Thus, the integrated photodetector has a low sensitivity to uncor-related radiation so that the output of the integrated photo-detector and thus element 121 contains mainly the Doppler-shifted signal.

The second information or signal 22 is obtained by means of the photodetector and the high-pass or band-pass filtering of filter 182 and the $1^{st}$ moment (of the spectrum) integrator 186.

The first information/signal 24 is obtained from the now separate detector 16 and the low-pass filter or band-pass filter 184 as described above.

Pre-amps 18 are illustrated. These are preferred, as the output signals from the detectors 121/16 are usually quite weak.

Figure 5A:
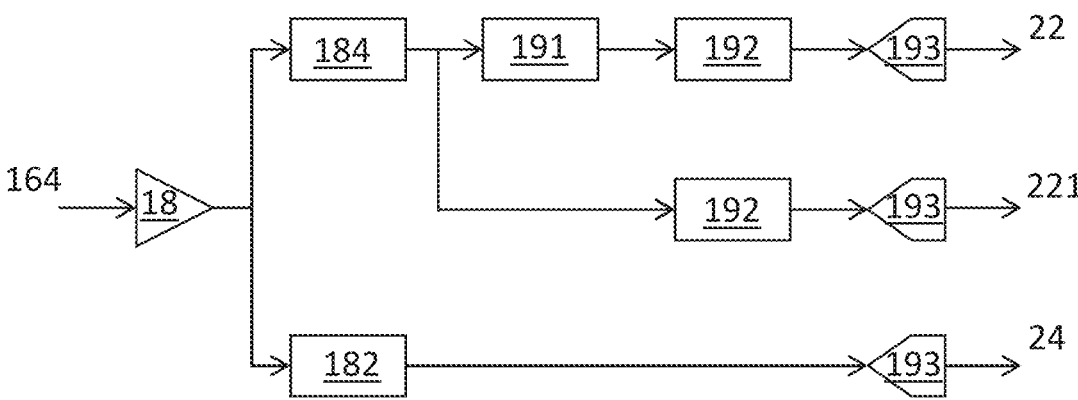
FIG. 5A and FIG. 5B illustrate analog and digital front-end signal processing.
Figure 5B:
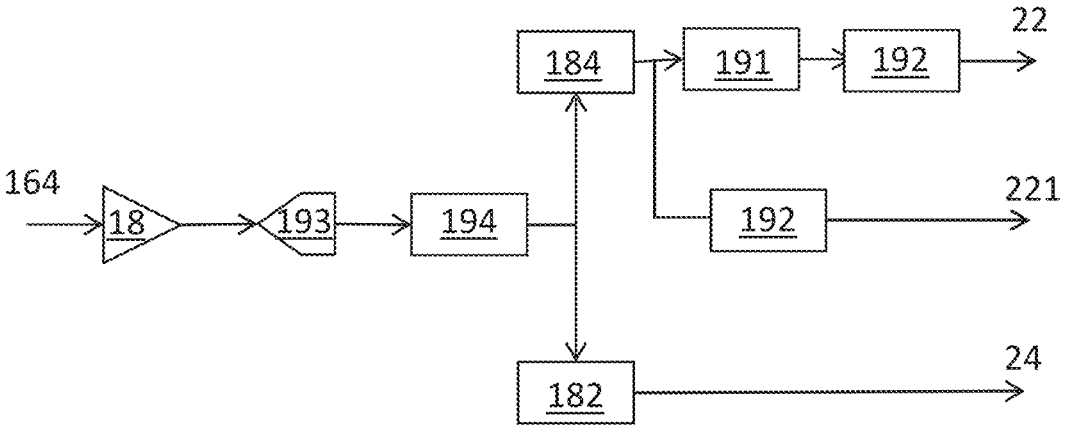

FIG. 5A and FIG. 5B show more detail on a useful front-end signal processing comprising, in FIG. 5A analog filtering and signal conditioning, and in FIG. 5B digital filtering and signal conditioning is seen.

In FIG. 5A, the detector output 164 is fed through optional pre-amplifier 18 to the filters 182/184, where the output of the filter 182 is fed to an optional AD converter (ADC) 193, if the further signal processing is desired in a digital setting.

The output of filter 184 is fed to an envelope detector 192 and then to an optional ADC 193 for outputting the $0^{th}$ moment of the differentiator 191. This, generally, is one form or portion of the first information or signal 22, here called 221. Alternatively, or additionally, the output of the filter 184 may be fed through a differentiator 191 before entering an envelope detector 192 and optionally being AD converted in converter 193. This provides an output being the $1^{st}$ moment which was also described above as an example of the second information or signal 22.

In FIG. 5B, the analog-to-digital conversion 193 is performed immediately after the preamp 18. The output signal of the ADC is fed to a Fast Fourier Transform element 194.

A digital version of the second information or signal 22 is obtained from the output of FFT element 194 by means of a filter 184 and a differentiator 191 and an envelope detector 192.

Optionally also a digital version of the $0^{th}$ moment of the second information or signal 221 may be obtained from the output signal of filter 184 by means of an envelope detector 192.

A digital version of the first information or signal 24 is obtained from the output of FFT element 194 by means of a filter 182.

Figure 6:
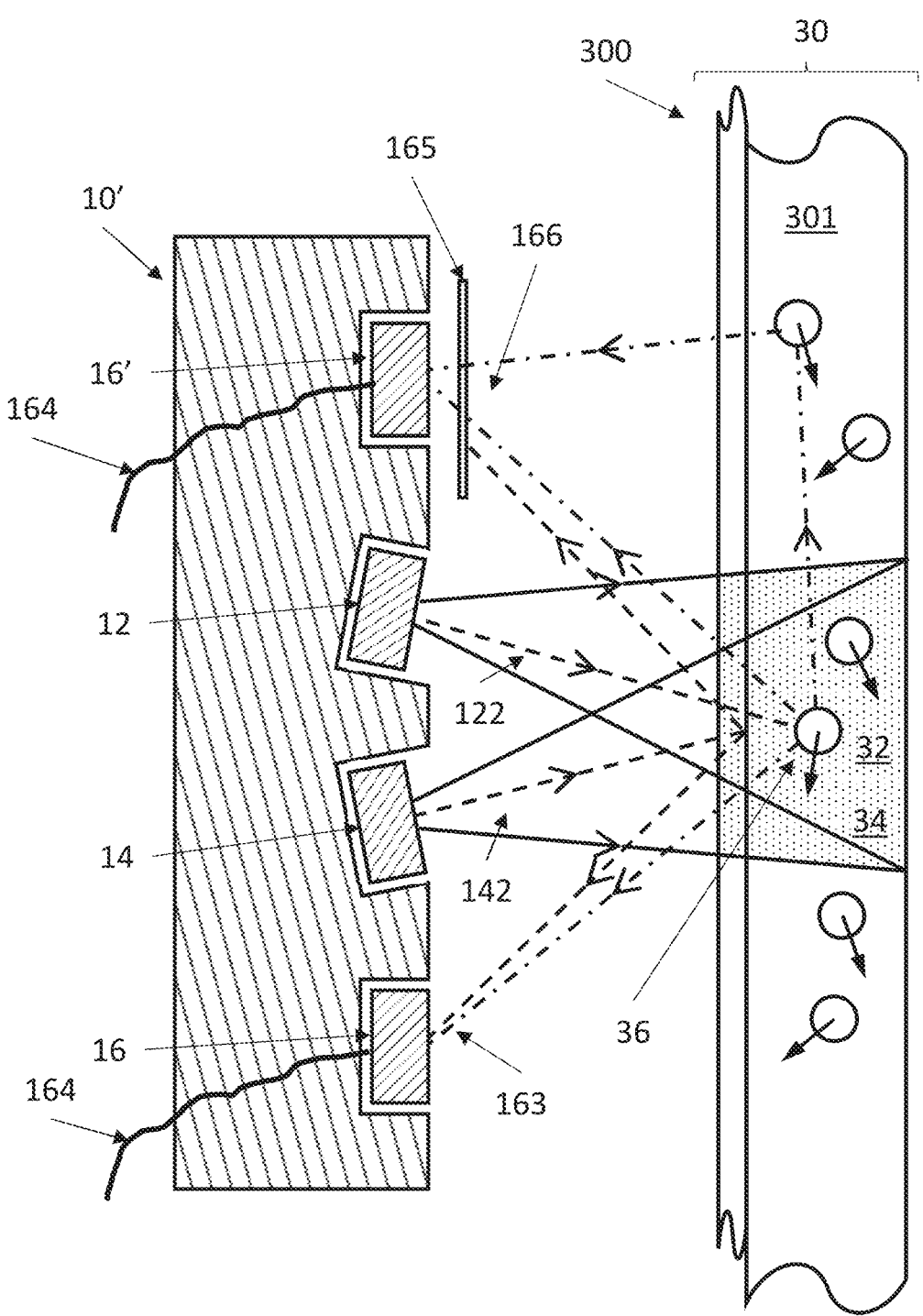
FIG. 6 illustrates a second embodiment of the device or system according to the invention.

FIG. 6 depicts another embodiment of the system or device of the invention. The body-worn device 10' comprises a coherent radiation source 12 (e.g. laser, VCSEL) and an incoherent radiation source 14 (e.g. LED), and, in this embodiment, two photodetectors 16 and 16' both configured to receive radiation or radiation, 163 and 166, respectively, from the illuminated tissue region. In contrast to the embodiment of FIG. 1, the radiation exposed tissue regions 32 and 34 now coincide. Then, both detectors 16/16' receive radiation originating from both sources 12/14 and scattered or Doppler shifted by discontinuities of optical properties in the tissue.

In front of the photodetector 16' an optional optical filter 165 is indicated. Also indicated are possible optical paths for scattered radiation and Doppler shifted radiation between the radiation sources 12/14 and the detectors 16/16'.

Figure 7:
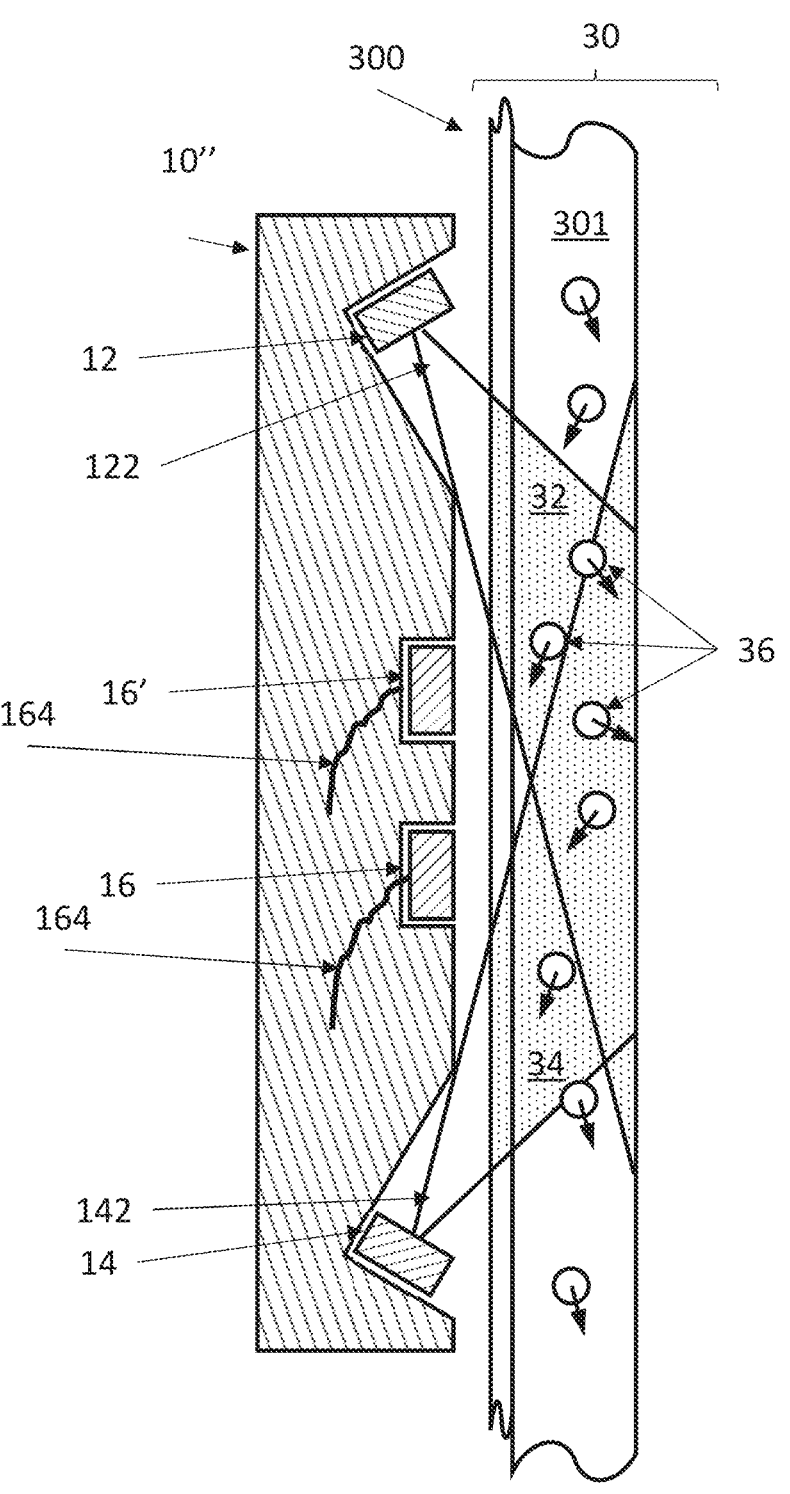
FIG. 7 illustrates a third embodiment of the device or system according to the invention.

FIG. 7 illustrates a similar embodiment wherein an overlap is seen between the illuminated tissue regions 32 and 34 and wherein two detectors 16 and 16' are illustrated. Only one detector is required, so one of the detectors may be left out. This configuration also allows one or both detectors to be fitted with optical filters so that specific wavelengths can be blocked. That embodiment may be operated as described in relation to FIGS. 1-4 and 5A-5B. Using two detectors is described with reference to FIG. 6.

Figure 8:
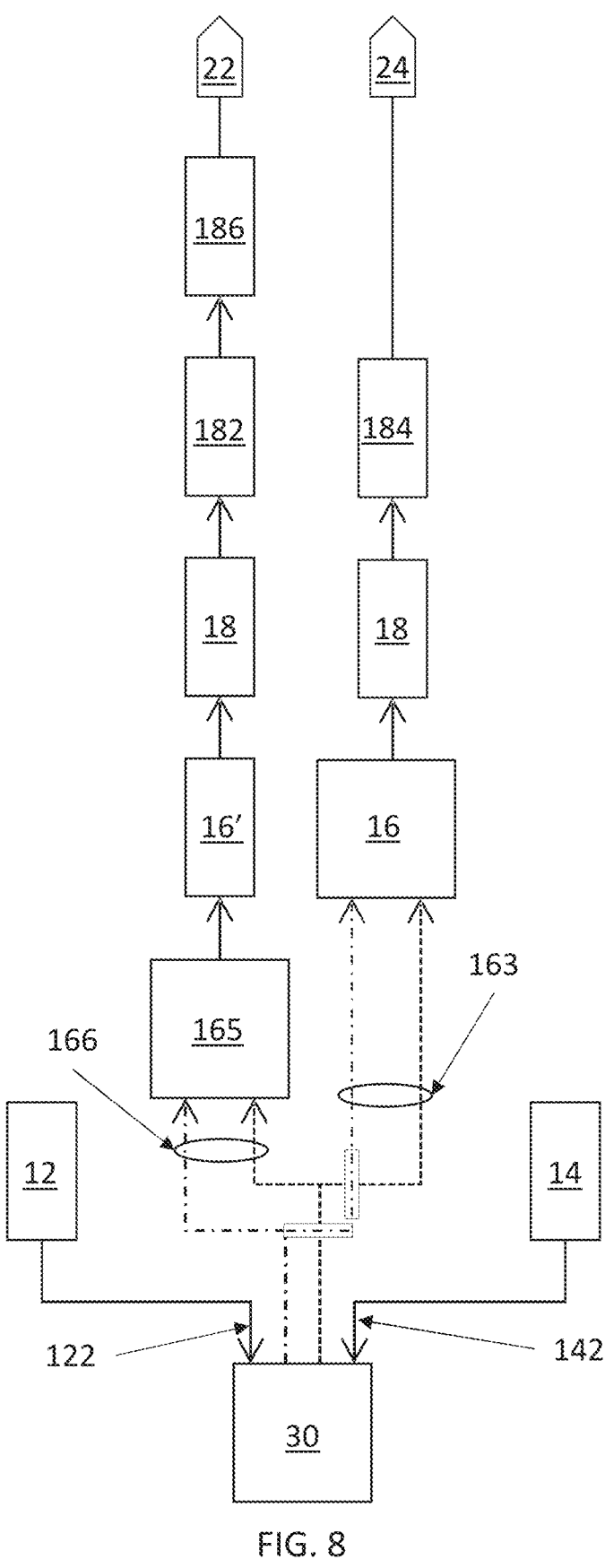
FIG. 8 illustrates an example of a front-end signal processing for a device according to e.g.

FIG. 8 depicts a block diagram for a suitable signals processing relating to the device/system of FIG. 6, where two photodetectors, 16 and 16', allow the use of an incoherent radiation source with a different wavelength than the coherent radiation source as well as the filtering of the radiation impinging on one detector. Since for small, low power lasers (e.g. VCSELs) the available wavelength range is limited, the easiest way of obtaining different wavelengths for the two sources is by selecting the source 14 with a different wavelength. Also signal processing can be easier if different wavelengths are used, for example if the LED 14 emits green radiation, a simple red filter 165 in front of the photodetector 16' would block any radiation originating from the source 14 and allow red or infrared light to pass. The first information or signal 24 may be obtained from the second photodetector 16 by means of a low-pass filter 184 connected to the output of pre-amp 18.

In this embodiment, pre-amps 18 are illustrated. These are optional but quite useful.

As seen also in e.g. FIG. 4, the second information or signal 22 may be derived from the detector 16' via a pre-amp 18, a filter 182 and the element 186 generating the $1^{st}$ moment of the output of the filter 182.

Figure 9:
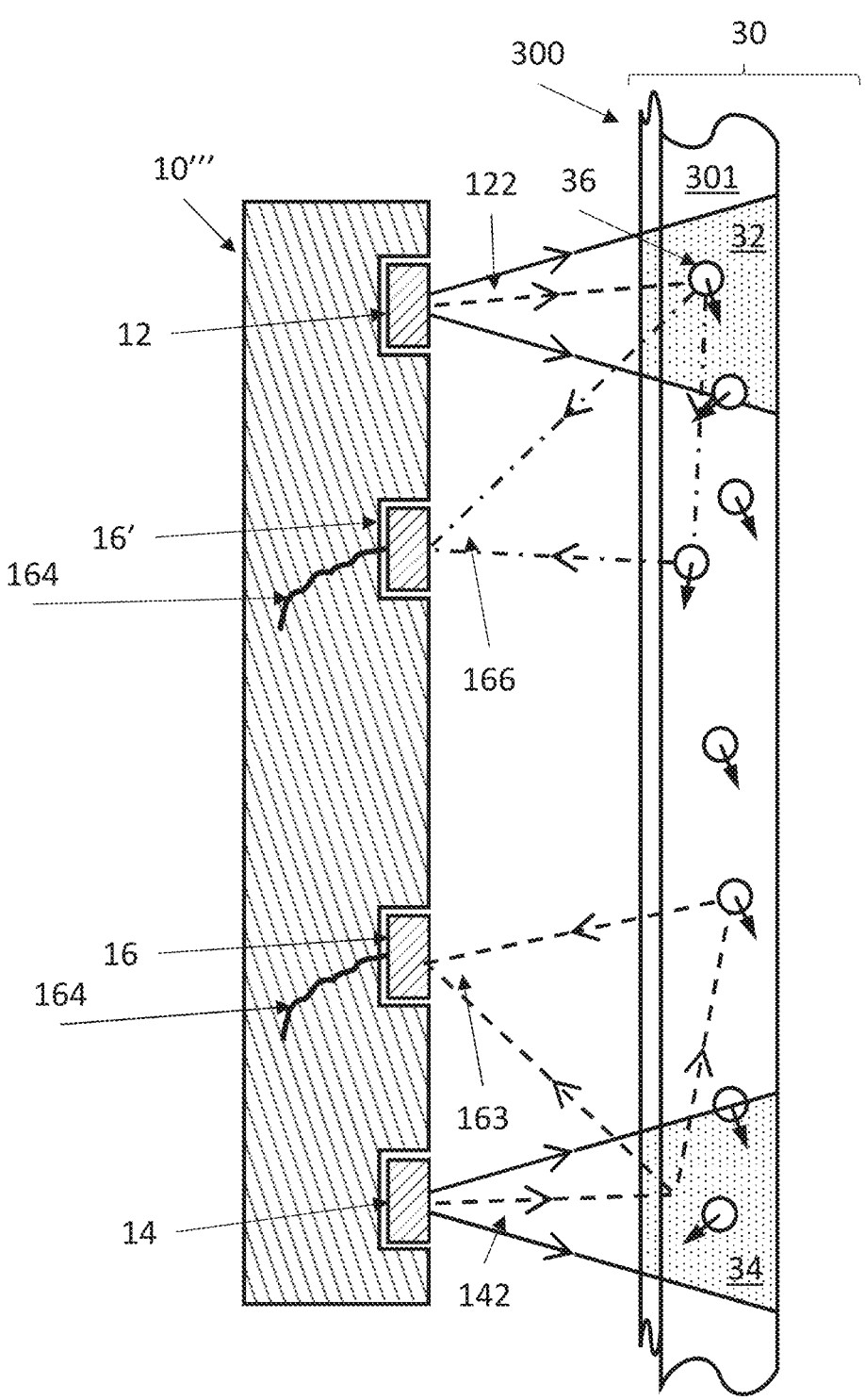

FIG. 9 illustrates yet an embodiment of the device or system according to the invention. In FIG. 9, compared to FIG. 6, the radiation sources 12, 14 are configured to each illuminate separate and non-overlapping tissue regions 32 and 34, respectively. Scattered and optionally also Doppler shifted radiation from region 32 is detected by the detector 16' and the scattered and optionally also Doppler shifted radiation from the region 34 is detected by the detector 16. No significant portion of the radiation from the source 12 reaches the detector 16 and no significant portion of the radiation from the source 14 reaches the detector 16'. In this situation, the above-described timing control and intermittent operation of the sources and/or the wavelength selection and optional filtering may be dispensed with, at there is no significant interference in one sensor from the other.

Figure 10:
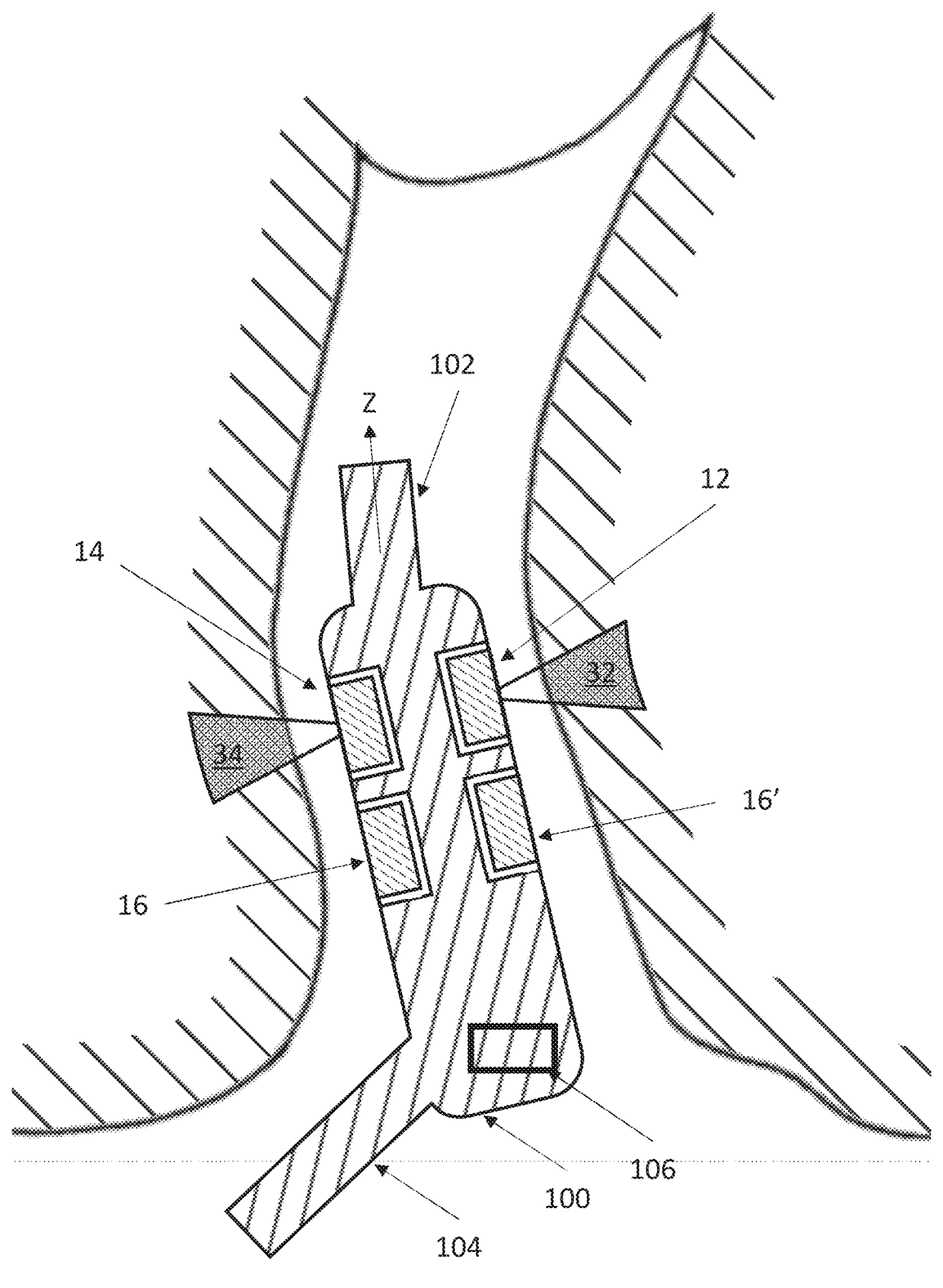
FIG. 10 illustrates a fifth embodiment of the device or system according to the invention for use in an ear canal.

FIG. 10 illustrates a particularly useful product comprising the system/device according to the invention. In principle, any embodiment of the device/system may be provided in this product, including any embodiment described in relation to the drawings. In the present situation, the product is a hearing aid or hearable for use in an ear canal of a person or animal. The product for this use has a cable 104 for receiving sound or signals to be converted into sound as well as a sound output 102, often in the form of a spout, for directing the sound toward the tympanic membrane of the pertaining ear. The cable 104 may also contain electrical connections for transmitting information such as the acquired first and second information or information derived therefrom. This product may comprise additional elements, such as a sound generator and/or a microphone (not illustrated), a controller/processor 106, or the like. The product may be held in place in the ear canal by a flexible dome (not illustrated).

The product 100 has a housing in which, or connected to which, the two radiation sources 12 and 14 are provided. In this embodiment, the two detectors 16 and 16' are used as the directions of the tissue regions 32 and 34 are selected to have no overlap.

The housing of the product 100 is configured to be provided in an elongated channel, so that the "no overlap" of the tissue regions 32/34 may be ensured or provided by having the sources 12/14 emit the radiation in opposite directions. Alternatively, the detectors 16, 16' may be positioned to receive radiation from opposite directions. Other directions than 180 degrees may be used, as may positions at different positions along the longitudinal axis, Z, of the housing of the product 100.

Naturally, the system/device/product may comprise windows, lenses, radiation guides or the like for guiding the radiation between the tissue and the sources and/or to the detector(s). Such optical elements may also be used for guiding the radiation, such as to define the size and position of the tissue regions by either controlling radiation from the sources and/or radiation from the tissue toward the detector(s).

In general, it is noted that the tissue regions 32/34, if desired non-overlapping, may not represent all of the volume of the tissue which receives radiation from the pertaining source 12/14. The detectors may be configured to receive radiation only from a portion of the volume actually illuminated, and when these portions are non-overlapping, the desired effect is obtained even though portions of the tissue actually receive radiation from both sources.

In general, the amplifiers, filters and the like described above and below for converting the output of the detector(s) into the first and second information/signals, may be handled by a processor, controller or the like provided at the sources, such as within a housing also holding the sources, detectors and potentially other elements.

The wavelengths used for the two sources 12/14 may be selected based on the final parameters of the blood which are desired determined.

The use of a shorter wavelength for the source 14 (e.g. a green LED) can be advantageous for measuring the first signal or information 24 since the absorption of green radiation in blood cells is larger than that of red or infrared radiation. Then, using green radiation, an increased sensitivity may be obtained for determining variations, such as pulsatility, of the amount of blood and thus of the blood perfusion.

Alternatively, a smaller wavelength difference between the coherent radiation source 12 (e.g. IR, 940 nm) and the incoherent source 14 (e.g. red, 660 nm, LED) can be advantageous to acquire additional biometrics on the oxygenation of the blood, since it is known that the absorption of oxygenized haemoglobin for IR is higher than for red radiation, while the absorption of non-oxygenized haemoglobin for red radiation is higher than for IR. In this case the optical filter in front of the photodetector could then block red radiation and pass infrared radiation.

In the embodiments above, several ways have been described of separating a first information/signal from a second information/signal in a device that acquires both from the same tissue region or from very near tissue regions. It may be obvious to combine details from these embodiments in other embodiments. For example we may think of using a multitude of LEDs with different wavelengths that are operated intermittently in order to acquire PPG signals with different characteristics. For example, SpO₂ determination typically involves a plurality of LEDs at different wavelengths to capture absorption differences between deoxyhemoglobin and oxyhemoglobin at different wavelengths, such as LEDs emitting radiation at 660 and 940 nm.

Having now a range of manners of obtaining the first and second information where the first information may be related to the volume or amount of blood in the tissue and the second information relates to a speed of the blood, different technologies and sensing techniques may be used for obtaining that information and different uses may be made of that information.

The first information may be determined using photo plethysmography (PPG) where radiation is fed into the tissue and an absorption thereof is determined. This information may be determined based on coherent radiation or incoherent radiation. The use of incoherent radiation is simpler as it is less sensitive to moving variations in density and/or refractive index in the tissue. Simple radiation sources would be LEDs but any type of radiation source, such as OLEDS, may be used and very simple detectors are easily implemented. Instead of backscatter PPG, transmission PPG may be employed. Any portion of the body of a user may be used, such as in the ear canal but also other portions or positions are useful, such as at a finger tip, ear pinna, earlobe, wrist or the like.

The second information may be derived from Doppler shifting of coherent radiation and may be obtained using a laser source, such as a laser diode, such as a VCSEL. VCSELs exist with built-in photodetector which detects radiation in the actual laser cavity, as is described above. Such sources are well suited for laser Doppler measurements and not the least for miniature setups. An alternative could be to utilize ultrasound Doppler for achieving this information.

The theory of the above-mentioned US20220133165 describes a PPG waveform as the superposition of incident and reflected waves, where the reflections are caused by impedance steps on mayor branches of the arterial system. Changes in blood pressure modify the wave propagation speed and consequently affect the time relation between the superpositioned waveforms.

The blood pressure related parameter can be derived from timing features in the PPG waveform that can be related to contributions from incident and reflected waves.

Three difficulties occur:

In case a noisy signal is acquired, the noise is amplified in each consecutive time derivation step. The noise makes it difficult to detect the peaks accurately;

In case the user has reduced arterial distensibility, due to aging and/or pathology, the amplitude of the PPG signal is reduced and thus more noisy;

Also in case of reduced arterial distensibility the wave propagation speed increases so that the incident and reflected waves overlap more and timing features become less pronounced.

These difficulties reduce the accuracy in PPG-based determination of the blood pressure related parameter for users for whom the accuracy matters most, namely elderly people and people with prevalence of hypertension.

However, when deriving not only this first information but also the second information, a more robust determination may be made as will be described in the following. For example, the signal to noise ratio (SNR) of the time-derivative of the first (typically PPG) signal may be improved by using the second (typically Laser Doppler Velocimetry—LDV) signal by means of a simple model that relates the blood flow speed to the blood pressure.

The first signal is proportional to the blood volume in the perfused tissue, which in turn depends on the distensibility of the arteries or arterioles. When distensibility degrades with age also the first signal deteriorates. On the other hand, the second signal is proportional to the blood flow speed which is less affected by distensibility.

The relation between the blood volume and the blood flow speed is determined by the (local) blood vessel impedance. This relation may be used to improve the first signal quality by using the second signal.

Both the first information (e.g. PPG) and the second information (e.g. LDV) acquired in the blood perfused tissue relate to the arterial blood pressure wave. Both relations are determined by vascular parameters such as diameter, length and distensibility of the connecting blood vessels. These relations can be expressed as transfer functions, that may be non-linear and may vary over time, both on a short term basis due to regulation of physiological mechanisms and on a long term basis such as due to aging or pathological changes.

Figure 11:
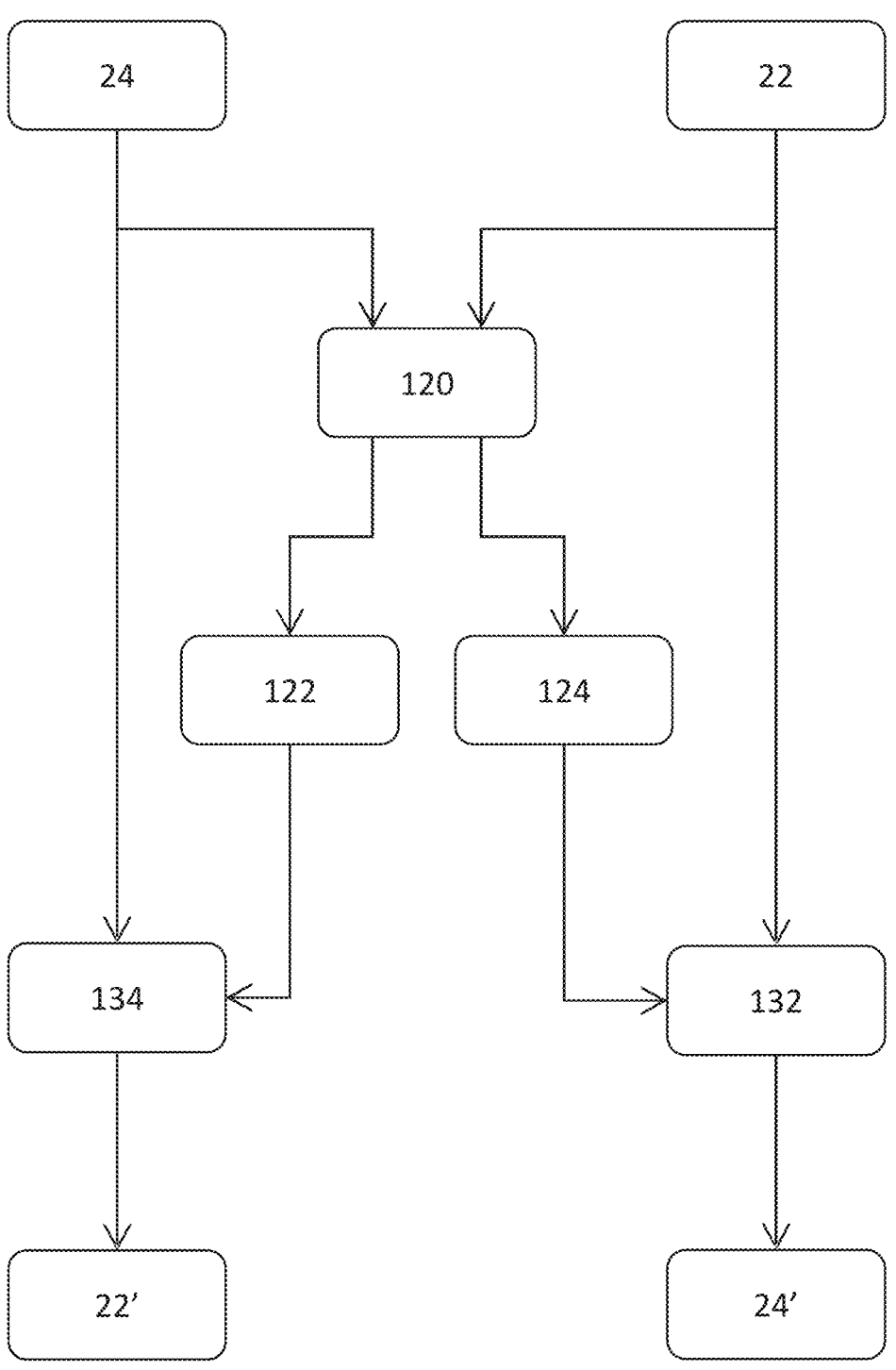
FIG. 11 illustrates generating synthetic first and second information from a model.

As a consequence, referring now to FIG. 11, the direct relationship between the first and second information (24 and 22, respectively) can be modelled by means of a more or less complex mathematical model 120. Such a model may be linear or nonlinear, deterministic or non-deterministic etc. An example of a linear model is a differential equation and another example is a non-deterministic model, such as one based on a deep learning model.

The simplest possible model that may be applicable is a first order linear differential equation (may be known as Windkessel model).

$$x_2(t) \approx c_0 + c_1 \cdot x_1(t) + c_2 \cdot x_1'(t)$$

wherein:
    $x_2(t)$ is the second information,
    $x_1(t)$ is the first information, $$x_1'(t)$$

is time derivative of the first information, and
    $c_n$ are the model parameters.

This model may be particularly accurate when the first and second information are acquired from overlapping tissue regions, more preferably from the same tissue region.

The model parameters may be time-dependent but do not vary within the timeframe of at least one heartbeat or that of a predetermined number of heartbeats or within a predetermined time span.

The model parameters may be calculated continuously over a shifting time window with a duration of at least one heartbeat, for example using a least mean square method.

Furthermore, representative values of the model parameters may be calculated continuously over the shifting time window. In particular, representative values of the model parameters may be calculated over a predetermined number of individual waveforms of the first and second information. The representative values of the model parameters are then used in the model to compute e.g. a synthetic derivative of the first information from the second information. For example, an average, median, mode, maximum or minimum of a given model parameter is used as representative value for that model parameter. In a first example, model parameters are computed for each individual waveform, and an average of the model parameters of a predetermined number of waveforms is computed. In a second example, an ensemble average of the waveform is computed (as described above), and model parameters are computed from the ensemble average.

For example, when using the Windkessel model above, the Windkessel coefficients (such as $c_0$, $c_1$, $c_2$ for the first order model) are computed as an average over a predetermined number of waveforms of the first information and corresponding waveforms of the second information. For example, coefficients are computed for each of a predetermined number of waveforms, and an average for each coefficient is computed. In another example, Windkessel coefficients are computed using an ensemble average of the first information and a corresponding ensemble average of the second information.

A reconstructed or synthetic version of the time derivative of the first information can now be determined as a function, particularly a weighted summation or linear function, of the first information and the second information according to:

$$xx_1'(t) = \frac{x_2(t) - c_0 - c_1 \cdot x_1(t)}{c_2}$$

30

Wherein $$xx_1'(t)$$

is a synthetic version of the time derivative of the first information.

One advantage of using the second information in addition to the first information in a model such as a Windkessel model is that the time derivative of the first information can be derived without a need to calculate a time derivative of the second and first information. This is particularly advantageous where the SNR of the time derivative of the first information is undesirably low, creating unreliable or unclear information from that time derivative, which in turn affects the accuracy of the determination of a physiological parameter.

Accordingly, according to a further preferred embodiment, the present invention provides a system wherein the controller is configured to:
    calculate a synthetic time derivative of the first information from the second information and the first information; and
    determine the physiological parameter from the synthetic time derivative of the first information.

According to another preferred embodiment, the present invention provides a system wherein the controller is configured to:
    calculate a synthetic time derivative of the first information from the second information and the first information;
    use the synthetic time derivative of the first information to calculate an improved first information; and
    determine the physiological parameter from the synthetic time derivative of the first information and first information and/or the improved first information.

According to yet another preferred embodiment, the present invention provides a system wherein the controller is configured to:
    calculate a time derivative of the first information from the second information and the first information;
    use the calculated time derivative of the first information and the first information to calculate an improved first information; and
    determine the physiological parameter from the improved first information.

According to another aspect, the present invention further provides a method wherein the step of determining the physiological parameter comprises:
    calculating a synthetic time derivative of the first information from the second information and the first information; and
    determining the physiological parameter from the synthetic time derivative of the first information.

According to another preferred embodiment, the present invention provides a method wherein the step of determining the physiological parameter comprises:
    calculating a synthetic time derivative of the first information from the second information and the first information;
    using the synthetic time derivative of the first information to calculate an improved first information; and
    determining the physiological parameter from the synthetic time derivative of the first information and first information and/or the improved first information.

According to yet another preferred embodiment, the present invention provides a method wherein the step of determining the physiological parameter comprises:

calculating a time derivative of the first information from the second information and the first information;

using the calculated time derivative of the first information and the first information to calculate an improved first information; and determining the physiological parameter from the improved first information.

According to one embodiment of the system and method, a Windkessel model is used to calculate the time derivative of the first information from the second information and the first information.

Depending on the accuracy needed a more complex model may be used, e.g. a higher order differential equation, or a non-linear differential equation, or a non-deterministic model, and a larger number of model parameters is determined.

In general, from the model, parameters may be generated for a first transfer function 122 and a second transfer function 124, which parameters may be performed in steps 134 and 132, respectively, for arriving at synthetic first and second information 24' and 22', respectively. Thus, the information 24' may be generated solely from the information 22 or partly therefrom, based on the model 120 and vice versa.

Figure 12A:
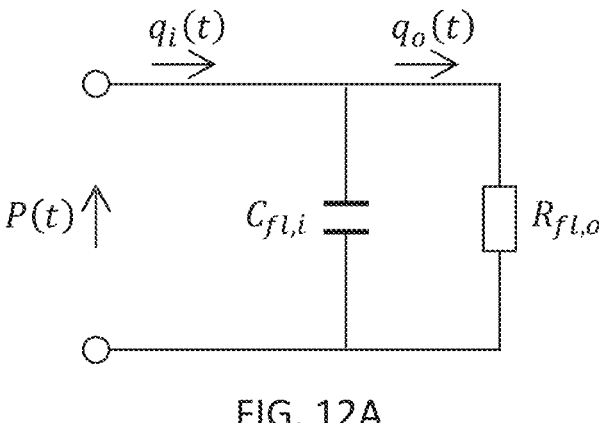
FIG. 12A, FIG. 12B, and FIG. 12C illustrate different Windkessel approximations.
Figure 12B:
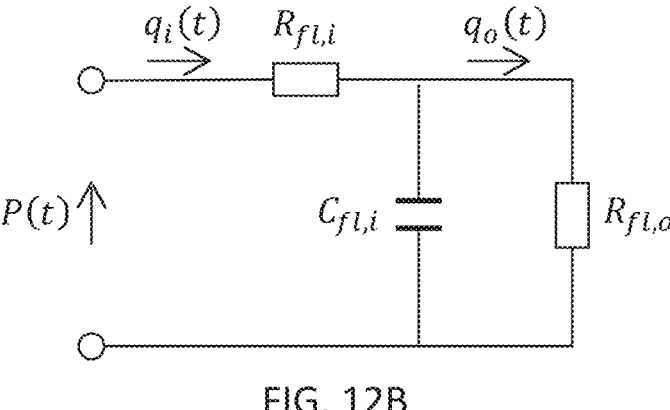
Figure 12C:
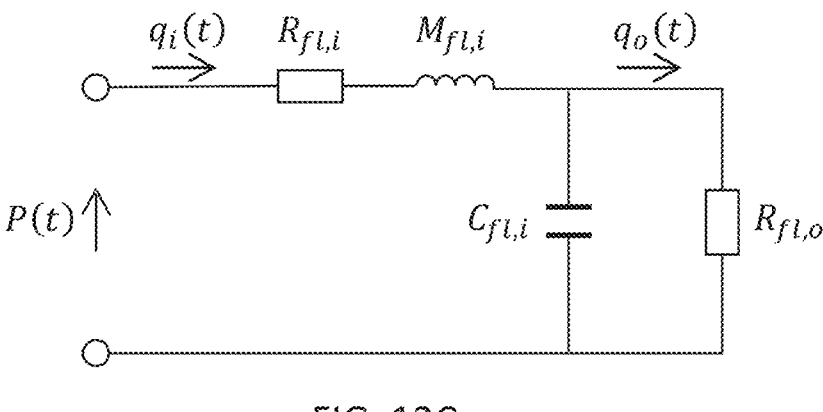

A Windkessel model can be represented as an electrical network, see FIG. 12A, FIG. 12B, and FIG. 12C. In this analogy, the charge in the capacitor represents the amount of blood in the tissue, and the input current represents the volume velocity of the blood, which is proportional to the speed. Since the charge is proportional to the capacitance and the voltage, the voltage across the capacitor is proportional to the blood pressure.

Since good results can already be obtained with a first order model, i.e. a two parameter Windkessel model, this will be elaborated in the following, although use of higher order models may improve the accuracy of the method, such as a second order model, i.e. a three parameter Windkessel model. Also, in the following, we will relate to the first information, which is proportional to the amount of blood in the blood perfused tissue and thus to the volumetric expansion, as PPG information and the second information as LDV information, where it is clear that this is an example only of how this information may be obtained.

The second order Windkessel model is depicted in FIG. 12A wherein:

$q_i(t)$ is the volumetric inflow, $C_{fl,i} \cdot P'(t)$ is the volumetric expansion rate, $P(t)/R_{fl,o}$ is the volumetric outflow, $P(t)$ is the (local) blood pressure, $P'(t)$ is the time derivative of the blood pressure, $C_{fl,i}$ is the effective fluidic compliance of the blood vessels, and $R_{fl,o}$ is the fluidic resistance of the downflow blood vessels.

The volumetric inflow is proportional to the average blood flow speed, which is proportional to the average Doppler shift measured by LDV. The average Doppler shift can be determined by taking the first moment of the spectral density of the photodetector output.

$$v(t) \propto M_1(t)$$

where the second information is normalized with respect to the amplitude of the photodetector output.

$$M_1(t) = \int_{f1}^{f2} f \cdot S_v(f, t)\, df$$

wherein:

$v(t)$ LDV signal, $M_1(t)$ is the first moment of the spectral density, $f_1$ and $f_2$ are the limits of the frequency band over which the first moment is calculated, and $S_v(f,t)$ is the spectral amplitude density of the photodetector output.

FIG. 12A illustrates a rather simple model, a two-element model. More complex models are seen in FIG. 12B, illustrating a three-element model, and FIG. 12C, illustrating a four-element model. The more elements, the better may the correlation with the blood flow be emulated. The skilled person will know how to alter the above formulas to include the additional elements.

Examples of measurement systems are seen in relation to FIGS. 1-4, 5A-5B, and 6-10 illustrating combined sensors for measuring the PPG signal $x(t)$ or first information 24 and for measuring the LDV signal $v(t)$ or second information 22.

As described above, the model parameters may be calculated continuously over a shifting time window with a duration of at least one heartbeat, for example using a least mean square method.

Depending on the accuracy needed a more complex model 120 may be used, e.g. a higher order differential equation, or a non-linear differential equation, or a non-deterministic model, and a larger number of model parameters is determined.

After the model parameters are determined, the parameters can be applied to a first transfer function 134 that calculates a synthetic version 22' of the second information 22 from the first information 24, and/or to a second transfer function 132 that calculates a synthetic version 24' of the first information 24 from the second information 22. This may in one embodiment be useful in case of temporary loss of one sensor, e.g. due to movement of the body comprising blood perfused tissue relative to the sensor, or temporary loss of signal quality, a poor signal to noise ratio, of either the first or the second information.

Using the same example of a first order linear differential equation, the first and second transfer functions may be written in the frequency domain as (ignoring DC levels):

$$F_1 = \frac{xx_2(\omega)}{x_1(\omega)} = c_1 + j\omega c_2$$

$$F_2 = \frac{xx_1(\omega)}{x_2(\omega)} = \frac{1}{c_1 + j\omega c_2}$$

wherein:

$j$ is the imaginary unit, $\omega = 2\pi f$ is the angular frequency, $xx_1(\omega)$ is a synthetic version of the first information, $x_1(\omega)$, and $xx_2(\omega)$ is a synthetic version of the second information, $x_2(\omega)$.

Depending on the model that was used to relate the first and second information, the transfer function may have more parameters, may be non-linear, or non-deterministic.

The physiological parameter, such as a systolic blood pressure or diastolic blood pressure, may be determined in many different ways. Various techniques for determining a physiological parameter from the first information are known in the art, e.g. determining a physiological parameter from a PPG signal. For example, determining the physiological parameter (e.g. blood pressure) comprises determining the timing of one or more characteristic features of the first information using a time derivative of the first information. Examples of characteristic features include systolic peak, and/or diastolic peak, and/or dicrotic notch and/or anacrotic notch. Additionally or alternatively, determining the physiological parameter (e.g. blood pressure) comprises determining one or more amplitudes and/or one or more areas of the first information (and/or second information), for example: amplitude of the systolic peak, amplitude of the diastolic peak, the area after the dicrotic notch, the area of the predetermined fraction of the signal.

Embodiments of the invention may use these known techniques to determine the physiological parameter. For example, the synthetic time derivative of the first information is used for determining timing of one or more characteristic features of the first information. Optionally, the first information is used for determining amplitudes or areas.

In another example, determining a physiological parameter comprises computing a time derivative of the first information, computing the synthetic version of the time derivative (as described above, e.g. using the Windkessel model) and adding these time derivatives to obtain an improved time derivative of the first information. For example, the addition comprises a weighted addition. The physiological parameter is then determined using this improved time derivative.

In yet another example, determining a physiological parameter comprises performing a numerical integration of the synthetic version of the time derivative of the first information, to obtain a synthetic version of the first information. The numerical integration may for example comprise integration using the trapezoid rule. The synthetic first information may then be added to the first information, after which the physiological parameter is derived from the result. For example, a weighted addition of the first information and the synthetic version of the first information is calculated, and the physiological parameter, such as blood pressure, is extracted from the result using known techniques, e.g. as used for PPG signals.

Typically, the first information and second information each comprise one or more discrete-time signals, each discrete-time signal comprising an array of samples at discrete time intervals. When calculating a weighted addition of the first information and the synthetic version thereof, different weights may be assigned to each sample of such discrete-time signals.

Figure 13:
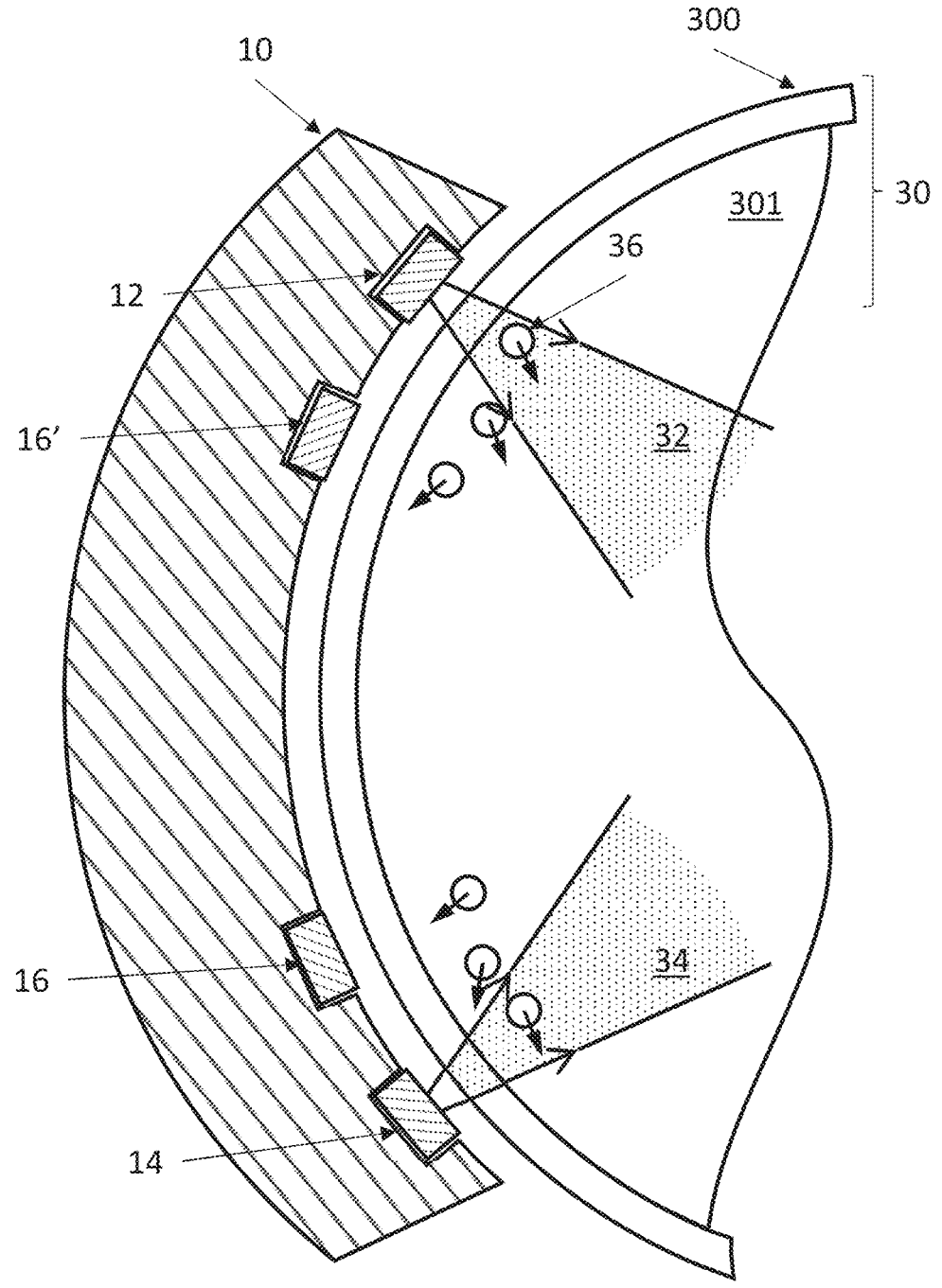
FIG. 13 illustrates a variant of the embodiment of FIG. 9, but with a curved shape of the device 10, so that is fits easier to the body for example on the wrist.

FIG. 13 illustrates another embodiment which, compared to that of FIG. 9, has a more rounded shape and thus is configured to fit around a portion of a rounded body part 300, such as a finger or an ear lobe. It is seen that the regions 32 and 34 are completely separate in this embodiment. This is merely a choice.

Figure 14:
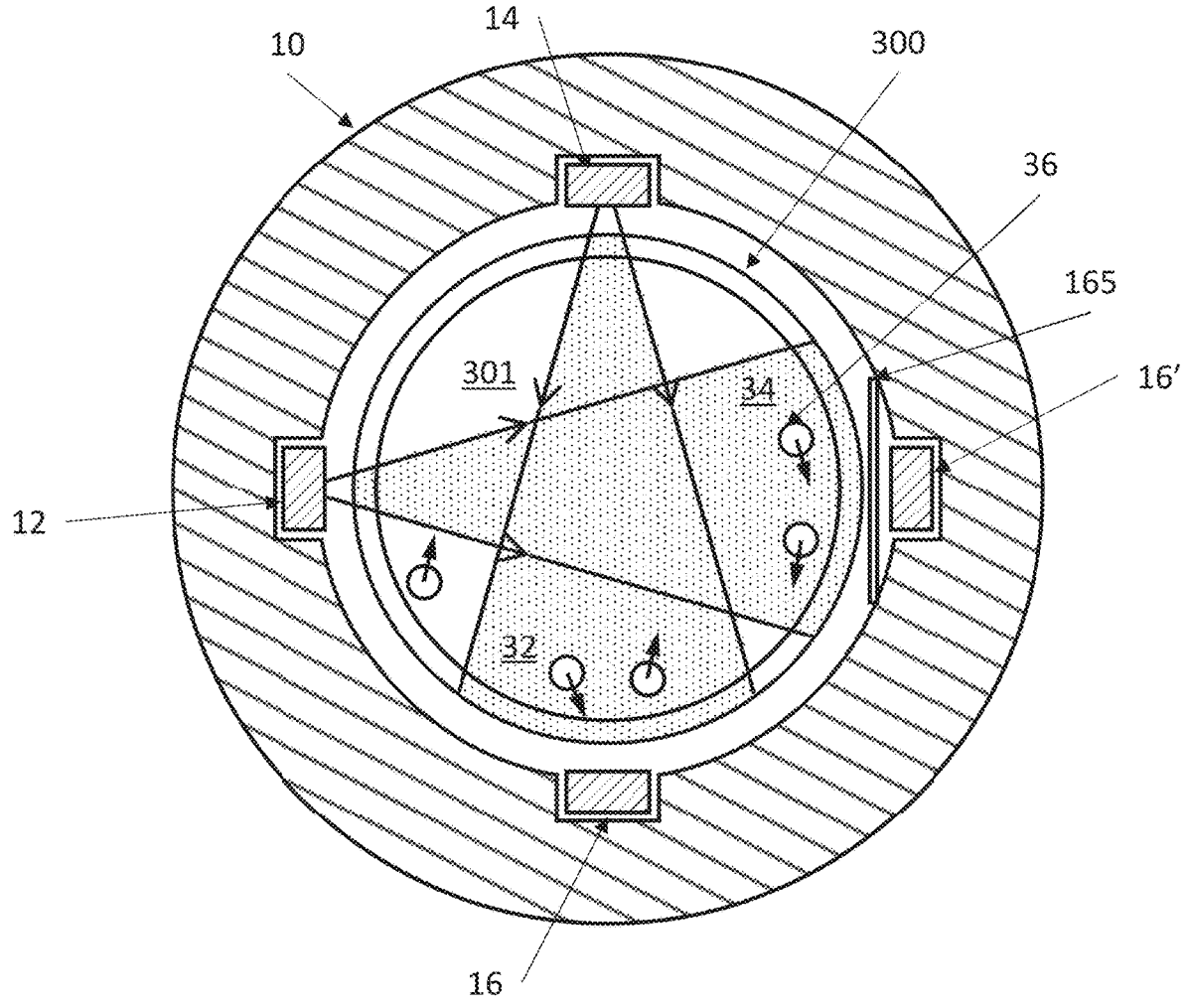
FIG. 14 illustrates an embodiment which may be worn around a body part, for example a finger.

FIG. 14 illustrates an embodiment having a cavity or channel inside which a body part 300, such as a finger or a limb, may be provided. In this embodiment, the regions 32 and 34 overlap.

Embodiments

1. A system for determining a physiological parameter of a body comprising blood perfused tissue, the system comprising:

a first sensor configured to receive first radiation from the blood perfused tissue and, based on the received first radiation, provide first information relating to an amount of blood in the tissue, a second sensor configured to receive second radiation from the blood perfused tissue and, based on the received second radiation, provide second information relating to a speed of blood in the tissue, a controller configured to calculate a first calculated signal from the second information and/or calculate a second calculated signal from the first information; use the first calculated signal and the first information to calculate an improved first information and/or use the second calculated signal and the second information to calculate an improved second information; and determine the physiological parameter from the improved first information and/or improved second information.

2. A system according to embodiment 1, wherein the controller is configured to calculate the first calculated signal using a model that predicts first information from second information and/or to calculate the second calculated signal using a model that predicts second information from first information.

3. A system according to embodiment 1 or 2, wherein the controller is configured to calculate the improved first information by adding the first calculated signal to the first information, preferably by weighted addition.

4. A system for determining a physiological parameter of a body comprising blood perfused tissue, the system comprising:

a first sensor configured to receive first radiation from the blood perfused tissue and, based on the received first radiation, provide first information relating to an amount of blood in the tissue, a second sensor configured to receive second radiation from the blood perfused tissue and, based on the received second radiation, provide second information relating to a speed of blood in the tissue, a controller configured to calculate a synthetic time derivative of the first information from the second information and the first information; and determine the physiological parameter from the synthetic time derivative of the first information.

5. A system according to embodiment 4, wherein the controller is configured to determine the physiological parameter from the synthetic time derivative of the first information and the first information.

6. A system according to embodiment 4 or 5, wherein the controller is configured to calculate the synthetic time derivative using a model that predicts a synthetic time derivative from first information and second information.

7. A system according to any of embodiments 1-3, wherein the controller is configured to calculate a synthetic time derivative of the first information and to calculate an improved first information from the synthetic time derivative of the first information and determine the physiological parameter from the improved first information.

8. A system according to any one of the preceding embodiments, wherein the controller is configured to determine blood pressure from the first and second information using a first-order or second-order Windkessel model.

9. A system according to any one of the preceding embodiments, wherein the first sensor comprises a radiation source configured to emit radiation into the tissue and wherein the first sensor is configured to determine the first information based on an amount of radiation absorbed and/or scattered in the tissue.

10. A system according to embodiment 9, wherein the first sensor is a PPG sensor.

11. A system according to any of the preceding embodiments, wherein the second sensor comprises a source of coherent radiation and, preferably, is capable of determining the second information based on a Doppler shift determination based on the second radiation.

12. A system according to any of the preceding embodiments, wherein the second sensor comprises a source of coherent radiation.

13. A system according to embodiment 12, wherein the first sensor comprises a source of incoherent radiation.

13. A system according to embodiment 12 or 13, wherein the second sensor comprises a VCSEL with integrated photodetector and wherein the first sensor comprises a radiation detector separate from the source of incoherent radiation.

14. A system according to any of embodiments 12-13, wherein the source of coherent radiation and the source of incoherent radiation are operated at the same time.

15. A system according to any of embodiments 12-14, wherein the source of coherent radiation is operated within a first number of time intervals and the source of incoherent radiation is operated within a second number of time intervals, where no second time interval overlaps with any first time interval.

16. A system according to any of the preceding embodiments, wherein the first sensor and the second sensor comprises a single detector configured to detect the first and second radiation.

17. A system according to any of the preceding embodiments, wherein the first sensor is configured to generate a first signal based on the received first radiation, low pass filtering or band pass filtering the first signal to provide a filtered first signal, and providing the first information based on the filtered first signal.

18. A system according to any of the preceding embodiments, wherein the second sensor is configured to generate a second signal based on the received second radiation, high pass filtering or band pass filtering the second signal to provide a filtered second signal and providing the second information based on the filtered second signal.

19. A system according to any of embodiments 12-15, wherein:
the second sensor is configured to receive the second radiation comprising radiation from the source of coherent radiation and to no substantial degree from the source of incoherent radiation, and, optionally the first sensor is configured to receive the first radiation comprising radiation from the source of incoherent radiation.

20. A system according to any of embodiments 12-15 and 19, wherein the source of coherent radiation and the source of incoherent radiation are configured to direct the coherent and incoherent radiation to same volume of blood perfused tissue and wherein the first sensor and the second sensor comprise one or more radiation detectors positioned to receive radiation from the volume.

21. A system according to any of embodiments 12-15, 19 and 20, wherein:
the source of coherent radiation is configured to emit the coherent radiation into a first volume of the blood perfused tissue,
the source of the incoherent radiation is configured to emit the incoherent radiation into a second volume of the blood perfused tissue, the first and second volumes being non-overlapping, and
the first sensor and the second sensor comprise one or more radiation detectors positioned to receive radiation from the first and second volumes.

22. A system according to any of the preceding embodiments, wherein:
the first sensor comprises a first radiation source and is configured to receive the first radiation from a first volume of the tissue,
the second sensor comprises a second radiation source and is configured to receive the second radiation from a second volume of the tissue, and
the first and second sensors are configured to have:
no more than 50%, such as no more than 35%, of the first radiation stem from the second radiation source and
no more than 50%, such as no more than 35%, of the second radiation stem from the first radiation source.

23. A system according to any of the preceding embodiments, the system further comprising a housing, wherein the first sensor is configured to receive the first radiation travelling in a first direction, where the second sensor is configured to receive the second radiation travelling in a second direction, and wherein the first direction is at least 90 degrees to the second direction.

24. A system according to embodiment 23, wherein the first and second directions penetrate the housing at opposite surfaces of the housing.

25. A system according to embodiment 23 or 24, which is configured to be provided in an ear, such as in an ear canal.

26. A system according to any of the preceding embodiments, wherein the controller is configured to adapt the first information based on the second information and determine the parameter from the adapted first information.

27. A system according to any of the preceding embodiments, wherein the controller is configured to adapt the second information based on the first information and determine the parameter from the adapted second information.

28. A system according to any of the preceding embodiments, wherein the parameter is heartrate, heart rate variability, breathing rate, peripheral oxygen saturation (SpO$_2$), blood perfusion of the tissue, blood flow speed, blood pressure, arterial distensibility, user motion detection, or user activity detection.

29. A system according to any of the preceding embodiments, wherein the controller is configured to determine the blood parameter from an equation comprising the first information and the second information as well as one or more calculated parameters.

30. A system according to embodiment 29, wherein the first information and/or the second information represents a periodic signal and where the controller is configured to calculate the calculated parameters from the first information and/or the second information for a period of time being at least a period of the periodic signal.

31. A system according to any of the preceding embodiments wherein:
   the first sensor comprises a first emitter configured to emit first radiation into the blood-perfused tissue;
   the second sensor comprises a second emitter configured to emit second, coherent, radiation into the blood-perfused tissue;
   the first and second sensors comprise at least one radiation detector configured to detect:
      scattered radiation from the blood-perfused tissue emitted by the second emitter and
      scattered radiation from the blood-perfused tissue emitted by the first emitter;
   the second sensor is configured to derive the second information based on a doppler shift in the scattered radiation,
   the first sensor is configured to derive the first information from intensity variation in the scattered radiation;
   the controller is configured to:
      calculate a first calculated signal from the second information and/or calculate a second calculated signal from the first information;
      use the first calculated signal and the first information to calculate an improved first information and/or use the second calculated signal and the second information to calculate an improved second information; and
      determine the physiological parameter from the improved first information and/or improved second information.
32. A system according to embodiment 31 wherein the controller is configured to:
   calculate a time derivative of the first information from the second information and the first information;
   use the calculated time derivative of the first information and the first information to calculate an improved first information; and
   determine the physiological parameter from the improved first information.
33. A system according to embodiment 32 wherein the controller is configured to calculate the time derivative of the first information from the second information and the first information using a Windkessel model, preferably a first or second order Windkessel model.
34. A system according to any of the preceding embodiments, wherein the second emitter is configured to emit a second coherent radiation having a wavelength in the near infra-red spectrum or infra-red spectrum, preferably the near infra-red spectrum.
35. A system according to any of the preceding embodiments, wherein the first emitter is configured to emit a first radiation having a wavelength in the green light spectrum, such as in the range of from 450 to 600 nm.
36. A system according to embodiment 35, wherein the first emitter is configured to emit a first radiation that is substantially monochrome.
37. A system according to any of the preceding embodiments, comprising at least two radiation detectors wherein a second radiation detector is configured to detect second scattered radiation from blood-perfused tissue radiated by the second coherent radiation and a first radiation detector is configured to detect first scattered radiation from blood-perfused tissue radiated by the first radiation.

38. A system according to any one of the preceding embodiments, wherein the second sensor is a laser Doppler velocimetry (LDV) detector.
39. A system according to any one of the preceding embodiments, wherein the first sensor is a photoplethysmography (PPG) detector.
40. A system according to any one of the preceding embodiments, wherein the signal processor is configured to calculate a first calculated signal from a second signal and add the first calculated signal to the first signal to calculate an improved first signal, having an improved signal to noise ratio relative to the first signal.
41. An apparatus for use in a system according to any one of the preceding embodiments, the apparatus comprising:
   A first sensor configured to emit first radiation into blood-perfused tissue of the body;
   A second sensor configured to emit second, coherent, radiation into blood-perfused tissue of the body, where the first and second sensors comprising at least one radiation detector configured to detect scattered radiation from the blood-perfused tissue radiated by the first radiation and/or the second coherent radiation; and
   a communication means configured for communicating information relating to the scattered radiation to a signal processor configured to derive a first signal from intensity variation in the scattered radiation and a second signal from a doppler shift in the scattered radiation.
42. An apparatus for use in a system according to any one of the preceding embodiments, the apparatus comprising:
   A first sensor configured to emit first radiation into blood-perfused tissue of the body;
   A second sensor configured to emit second, coherent, radiation into blood-perfused tissue of the body;
   the first and second sensors comprising at least one radiation detector configured to detect scattered radiation from blood-perfused tissue radiated by the first radiation and/or the second coherent radiation;
   A signal processor configured to derive a first signal from intensity variation in the scattered radiation and a second signal from a doppler shift in the scattered radiation; and
   a communication means configured for communicating the first signal and the second signal to a signal processor configured to calculate a first calculated signal from a second signal and/or calculate a second calculated signal from a first signal and use the first calculated signal and the first signal to calculate an improved first signal and/or use the second calculated signal and the second signal to calculate an improved second signal.
43. An apparatus for use in a system according to any one of the preceding embodiments, the apparatus comprising:
   A second sensor configured to emit second, coherent, radiation into blood-perfused tissue of the body;
   A first sensor configured to emit first radiation into blood-perfused tissue of the body, where the first and second sensors comprise at least one radiation detector configured to detect scattered radiation from blood-perfused tissue radiated by the second coherent radiation and/or the first radiation;
   A signal processor configured to derive a first signal from intensity variation in the scattered radiation and a second signal from a doppler shift in the scattered radiation; to calculate a first calculated signal from the second signal and/or calculate a second calculated signal from the first signal and use the first calculated signal and the first signal to calculate an improved first signal and/or use the second calculated signal and the second signal to calculate an improved second signal; and communication means configured for communicating the improved first signal and/or the improved second signal to a controller configured to determine the physiological parameter from the improved first signal and/or improved second signal.

44. An apparatus for determining a physiological parameter of a body comprising blood perfused tissue, the apparatus comprising:

a photoplethysmography (PPG) sensor configured to provide a PPG signal relating to an amount of blood in the tissue; and a laser Doppler velocimetry (LDV) sensor configured to provide an LDV signal relating to a speed of blood in the tissue, wherein the LDV sensor preferably comprises a Vertical Cavity Surface-Emitting Laser (VCSEL).

45. The apparatus of embodiment 44, further comprising a controller configured to determine the physiological parameter from the PPG signal and LDV signal.

46. The apparatus of embodiment 45, wherein the controller is configured as described in any of the embodiments 1-43.

47. The apparatus of embodiment 44, further comprising communication means configured for communicating the PPG signal and LDV signal to a controller for determining the physiological parameter from the PPG signal and the LDV signal, preferably wherein the apparatus is intended for use in a system according to any of the embodiments 1-43.

48. The apparatus of any one or more of embodiments 44-47, wherein the PPG sensor comprises a source of incoherent radiation and the LDV sensor comprises a source of coherent radiation, wherein the radiation sources are configured to each illuminate separate and non-overlapping tissue regions.

49. Apparatus according to any one of the above embodiments, wherein the apparatus is a wearable.

50. A method of determining a physiological parameter of a body comprising blood perfused tissue, the method comprising:

providing first information from a first sensor receiving first radiation from the blood perfused tissue, the first information relating to an amount of blood in the tissue, providing second information from a second sensor receiving second radiation from the blood perfused tissue, the second information relating to a speed of blood in the tissue, and determining the physiological parameter by:

calculating a first calculated signal from the second information and/or calculating a second calculated signal from the first information;

using the first calculated signal and the first information to calculate an improved first information and/or using the second calculated signal and the second information to calculate an improved second information; and determining the physiological parameter from the improved first information and/or improved second information.

51. A method of determining a physiological parameter of a body comprising blood perfused tissue, the method comprising:

providing first information from a first sensor receiving first radiation from the blood perfused tissue, the first information relating to an amount of blood in the tissue, providing second information from a second sensor receiving second radiation from the blood perfused tissue, the second information relating to a speed of blood in the tissue, and determining the physiological parameter by:

calculating a synthetic time derivative of the first information from the second information and the first information; and determining the physiological parameter from the synthetic time derivative of the first information.

52. A method according to embodiment 50 or 51, wherein the step of proving the first information comprises:

controlling a radiation emitter to emit radiation into the tissue and determining the first information based on an amount of radiation absorbed and/or scattered in the tissue.

53. A method according to embodiment 52, wherein the step of providing the first information comprises providing PPG information.

54. A method according to any of embodiments 50-53, wherein the step of providing the second information comprises:

controlling a source of coherent radiation to emit coherent radiation into the tissue and determining the second information based on a Doppler velocity or Doppler shift determination based on the second radiation.

55. A method according to any of embodiments 50-54, wherein the second sensor and the first sensor output coherent radiation and incoherent radiation.

56. A method according to embodiment 55, wherein the second sensor comprises a VCSEL with integrated photodetector and wherein the first sensor comprises a radiation detector separate from the integrated photodetector.

57. A method according to any of embodiments 55 and 56, wherein the coherent radiation and the incoherent radiation is emitted at the same time.

58. A method according to any of embodiments 55 and 56, wherein the coherent radiation is emitted within a first number of time interval and wherein the incoherent radiation is emitted within a second number of time intervals, where no second time interval overlaps with any first time interval.

59. A method according to any of embodiments 55-58, wherein the determining step comprises a single detector detecting the first and second radiation.

60. A method according to any of embodiments 50-59, wherein the step of providing the first information comprises generating a first signal based on the received first radiation and low pass filtering the first signal.

61. A method according to any of embodiments 50-60, wherein the step of providing the second information comprises generating a second signal based on the received second radiation and high pass filtering the second signal.

62. A method according to any of embodiments 55-59, wherein:
the first radiation comprises radiation from the incoherent radiation and
the second radiation comprises radiation from the coherent radiation and to no substantial degree any of the incoherent radiation.
63. A method according to any of embodiments 55-59 and 62, wherein the coherent radiation and the incoherent radiation is directed to same volume of blood perfused tissue and wherein the first sensor and the second sensor comprise one or more radiation detectors positioned to receive radiation from the volume.
64. A method according to any of embodiments 55-59, 62 and 63, wherein:
the coherent radiation is emitted into a first volume of the blood perfused tissue,
the incoherent radiation is emitted into a second volume of the blood perfused tissue, the first and second volumes being non-overlapping, and
the first sensor and the second sensor comprise one or more radiation detectors positioned to receive radiation from the first and second volumes.
65. A method according to any of embodiments 50-64, wherein:
the step providing the first information comprises operating a first sensor to receive the first radiation from a first volume of the tissue,
the step of proving the second information comprises operating a second sensor to receive the second radiation from a second volume of the tissue, and
the first and second sensors have:
no more than 50% such as no more than 35% of the first radiation stemming from the second radiation source and
no more than 50% such as no more than 35% of the second radiation stemming from the first radiation source.
66. A method according to any of embodiments 50-65, wherein:
the step of providing the first information comprises receiving the first radiation where the first radiation travels in a first direction,
the step of providing the second information comprises receiving the second radiation where the second radiation travels in a second direction, and wherein the first direction is at least 90 degrees to the second direction.
67. A method according to embodiment 66, wherein the first and second radiation penetrate the housing at opposite surfaces of the housing.
68. A method according to any of embodiments 50-67, wherein the determining step comprises adapting the first information based on the second information and determining the parameter from the adapted first information.
69. A method according to any of embodiments 50-68, wherein the determining step comprises adapting the second information based on the PPG information and determining the parameter from the adapted second information.
70. A method according to any of embodiments 50-69, wherein the parameter is heartrate, heart rate variability, breathing rate, peripheral oxygen saturation (SpO$_2$), blood perfusion of the tissue, blood flow speed, blood pressure, arterial distensibility, user motion detection, or user activity detection.

71. A method according to any of embodiments 50-70, wherein the determining step comprises determining the blood parameter from an equation comprising the first information and the second information as well as one or more calculated parameters.
72. A method according to embodiment 71, wherein the first information and/or the second information represents a periodic signal and where the calculated parameters are calculated from the first information and/or the second information for a period of time being at least a period of the periodic signal.
73. A method according to any of embodiments 50-72, wherein:
the step of providing the first information comprises a first emitter of the first sensor emitting first radiation into the blood-perfused tissue;
the step of providing the second information comprises a second emitter of the second sensor emitting a second, coherent, radiation into the blood-perfused tissue;
the steps of providing the first and second information comprise detecting:
scattered radiation from the blood-perfused tissue emitted by the second emitter and
scattered radiation from the blood-perfused tissue emitted by the first emitter;
the step of providing the second information comprises deriving the second information based on a doppler shift in the scattered radiation,
the step of providing the first information comprises deriving the first information from intensity variation in the scattered radiation;
the step of determining the parameter comprises:
calculating a first calculated signal from the second information and/or calculating a second calculated signal from the first information;
using the first calculated signal and the first information to calculate an improved first information and/or using the second calculated signal and the second information to calculate an improved second information; and
determining the physiological parameter from the improved first information and/or improved second information.
74. A method according to embodiment 73, wherein the step of determining the physiological parameter comprises:
calculating a time derivative of the first information from the second information and the first information;
using the calculated time derivative of the first information and the first information to calculate an improved first information; and
determining the physiological parameter from the improved first information.
75. A method according to embodiment 74 wherein a Windkessel model is used to calculate the time derivative of the first information from the second information and the first information.
76. A computer program comprising instructions which, when executed by a computing device or system, cause said computing device or system to execute the method of any of the embodiments 50-75.
77. A computer-readable medium storing the computer program of embodiment 76.

US 12,605,079 B2

43

The invention claimed is:

1. A system for determining a physiological parameter of a body comprising blood perfused tissue, the system comprising:

a photoplethysmography sensor (PPG sensor) configured to receive first radiation from the blood perfused tissue and, based on the received first radiation, provide first information relating to an amount of blood in the blood perfused tissue, wherein the first radiation is radiation in a wavelength interval of 450 nm to 1000 nm, a laser Doppler velocimetry sensor (LDV sensor), the LDV sensor including a source of coherent radiation, the LDV sensor configured to receive second radiation from the blood perfused tissue based on the source emitting the coherent radiation to the blood perfused tissue and, based on the received second radiation, provide second information relating to a speed of blood in the blood perfused tissue, wherein the second radiation is radiation in a wavelength interval of 700 nm to 1000 nm, and a controller configured to:

calculate a prediction a time derivative of the first information from both the second information and the first information, as an output of a model that predicts the time derivative of the first information relating to the amount of blood in the blood perfused tissue from both the first information relating to the amount of blood in the blood perfused tissue and the second information relating to the speed of blood in the blood perfused tissue;

determine the physiological parameter from the prediction of the time derivative of the first information, wherein the physiological parameter includes blood pressure; and cause the physiological parameter to be output, illustrated, indicated, or any combination thereof.

2. The system according to claim 1, wherein the controller is configured to determine the physiological parameter from the prediction of the time derivative of the first information and the first information.

3. The system according to claim 1, wherein the prediction of the time derivative is calculated as a linear function of the first information and the second information.

4. The system according to claim 1, wherein the controller is configured to determine the blood pressure from the first information and the second information using a first-order or second-order Windkessel model.

5. The system according to claim 1, wherein the PPG sensor comprises a radiation source configured to emit radiation into the blood perfused tissue and wherein the PPG sensor is configured to determine the first information based on an amount of radiation absorbed and/or scattered in the blood perfused tissue.

6. The system according to claim 1, wherein the PPG sensor comprises a source of incoherent radiation.

7. The system according to claim 1, wherein the LDV sensor is configured to determine the second information based on a Doppler shift determination based on the second radiation.

8. The system according to claim 1, wherein:

the PPG sensor comprises a first emitter configured to emit a particular radiation into the blood perfused tissue;

the LDV sensor comprises a second emitter configured to emit the coherent radiation into the blood perfused tissue;

the PPG sensor and the LDV sensor comprise at least one radiation detector configured to detect:

scattered radiation from the blood perfused tissue, based on the coherent radiation emitted by the second emitter; and scattered radiation from the blood perfused tissue, based on the particular radiation emitted by the first emitter;

the LDV sensor is configured to derive the second information based on a doppler shift in the scattered radiation; and the PPG sensor is configured to derive the first information from intensity variation in the scattered radiation.

9. A wearable device comprising the system of claim 1.

10. A method of using a system for determining a physiological parameter of a body comprising blood perfused tissue, the method comprising:

providing first information relating to an amount of blood in the blood perfused tissue from a photoplethysmography sensor (PPG sensor) of the system, based on the PPG sensor receiving first radiation from the blood perfused tissue, wherein the first radiation is radiation in a wavelength interval of 450 nm to 1000 nm, providing second information relating to a speed of blood in the blood perfused tissue from a laser Doppler velocimetry sensor (LDV sensor) of the system, the LDV including a source of coherent radiation, the providing of the second information based on the LDV sensor receiving second radiation from the blood perfused tissue, the LDV sensor receiving the second radiation based on the source emitting the coherent radiation to the blood perfused tissue, wherein the second radiation is radiation in a wavelength interval of 700 nm to 1000 nm, and determining, by a controller of the system, the physiological parameter by:

calculating a prediction of a time derivative of the first information from both the second information and the first information, as an output of a model that predicts the time derivative of the first information relating to the amount of blood in the blood perfused tissue from both the first information relating to the amount of blood in the blood perfused tissue and the second information relating to the speed of blood in the blood perfused tissue; and determining the physiological parameter from the prediction of the time derivative of the first information, wherein the physiological parameter includes blood pressure; and causing, by the controller of the system, the physiological parameter to be output, illustrated, indicated, or any combination thereof.

11. The method according to claim 10, wherein the physiological parameter is determined from the prediction of the time derivative of the first information and the first information.

12. The method according to claim 10, wherein:

the providing of the first information comprises a first emitter of the PPG sensor emitting a particular radiation into the blood perfused tissue;

the providing of the second information comprises a second emitter of the LDV sensor emitting the coherent radiation into the blood perfused tissue;

the providing of the first information and the second information comprise detecting:

scattered radiation from the blood perfused tissue, based on the coherent radiation emitted by the second emitter; and scattered radiation from the blood perfused tissue, based on the particular radiation emitted by the first emitter;

the providing of the second information comprises deriving the second information based on a doppler shift in the scattered radiation; and the providing of the first information comprises deriving the first information from intensity variation in the scattered radiation.

13. A computer-readable medium storing a computer program comprising instructions which, when executed by a computing device or system, cause said computing device or system to execute a method, the method comprising:

obtaining first information relating to an amount of blood in blood perfused tissue from a photoplethysmography sensor (PPG sensor), based on the PPG sensor receiving first radiation from the blood perfused tissue, wherein the first radiation is radiation in a wavelength interval of 450 nm to 1000 nm, obtaining second information relating to a speed of blood in the blood perfused tissue from a laser Doppler velocimetry sensor (LDV sensor), the LDV sensor including a source of coherent radiation, the second information obtained from the LDV sensor based on the LDV sensor receiving second radiation from the blood perfused tissue, the LDV sensor receiving the second information based on the source emitting the coherent radiation to the blood perfused tissue, wherein the second radiation is radiation in a wavelength interval of 700 nm to 1000 nm, and determining a physiological parameter by:

calculating a prediction of a time derivative of the first information from both the second information and the first information, as an output of a model that predicts the time derivative of the first information relating to the amount of blood in the blood perfused tissue from both the first information relating to the amount of blood in the blood perfused tissue and the second information to the speed of blood in the blood perfused tissue; and determining the physiological parameter from the prediction of the time derivative of the first information; and causing the physiological parameter to be output, illustrated, indicated, or any combination thereof.

* * * * *